United States Patent [19]
Hastrup et al.

[11] Patent Number: 5,702,934
[45] Date of Patent: *Dec. 30, 1997

[54] PROCESSES FOR PRODUCING AN ENZYME

[75] Inventors: Sven Hastrup, København V.; Sven Branner, Lyngby; Birthe Ravn Jørgensen, Søborg; Tove Christensen, Lyngby; Birgitte Bojer Jørgensen, Kokkedal, all of Denmark; Jeffrey R. Shuster, Davis, Calif.; Mark Madden, Pleasant Hill, Calif.; Donna L. Moyer, Davis, Calif.; Claus Fuglsang, Copenhaven NV, Denmark

[73] Assignees: Novo Nordisk A/S, Bagsvaerd, Denmark; Novo Nordisk Biotech, Inc., Davis, Calif.

[ * ] Notice: The term of this patent shall not extend beyond the expiration date of Pat. No. 5,693,520.

[21] Appl. No.: 238,130

[22] Filed: May 4, 1994

[30] Foreign Application Priority Data

May 5, 1993 [DK] Denmark .................. 522/93

[51] Int. Cl.$^6$ .................. C12N 9/00; C12N 9/76; C12N 9/58; C12N 1/15
[52] U.S. Cl. .................. 435/183; 435/69.1; 435/68; 435/71.1; 435/172.3; 435/183; 435/213; 435/223; 435/252.3; 435/252.33; 435/252.31; 435/252.35; 435/254.11; 435/254.21; 435/254.7; 435/254.3; 435/320.1; 536/23.2; 935/14; 935/28; 935/34; 935/56; 935/68
[58] Field of Search .................. 435/69.1, 69.3, 435/69.8, 71.1, 71.2, 172.3, 183, 189, 233, 252.3, 252.31, 252.33, 254.11, 254.21, 254.7, 254.3, 320.1, 213, 223, 68; 536/23.2; 935/14, 28, 34, 56, 68

[56] References Cited

U.S. PATENT DOCUMENTS

| | | | |
|---|---|---|---|
| 3,652,399 | 3/1972 | Isono et al. .................. | 195/62 |
| 5,077,204 | 12/1991 | Brake et al. .................. | 435/68 |
| 5,288,627 | 2/1994 | Nielsen et al. .................. | 435/232 |

FOREIGN PATENT DOCUMENTS

| | | |
|---|---|---|
| 0319944 | 6/1989 | European Pat. Off. . |
| WO 91/06314 | 5/1991 | WIPO . |
| 9425583 | 11/1994 | WIPO . |

OTHER PUBLICATIONS

Baker et al., Proteins: Structure, Function, and Genetics 12:339–344 (1992).
Epstein et al., Jour. Biol. Chemistry, vol. 263, No. 32, pp. 16586–16590 (1988).
Jaton–Ogay et al., EMBL Data Library Entry S42894 (1994).
Tatsumi et al., Mol. Gen. Genet 228:97–103 (1991).
Nakadai, et al., Agr. Biol. Chem., vol. 37, No. 12, pp. 2695–2701 (1973).
Sekine, H., Agr. Biol. Chem., vol. 36, No. 2, pp. 207–216 (1972).
Pollock et al., Rapid Communications, Metalloprotease Mediation of Big Endothelin Effects in Vivo, pp. R257–R263 (1991).
Macfarlane et al., Applied and Environmental Microbiology, vol. 58, No. 4, pp. 1195–1200 (1992).
Sekine, H., Agr. Biol. Chem., vol. 36, No. 12, pp. 2143–2150 (1972).
Malardier et al., Gene, vol. 78, pp. 147–156 (1989).
Noma et al., Nature, vol. 319, pp. 640–646 (1986).
Sekine, H., Agr. Biol. Chem. vol. 37, No. 8, pp. 1945–1952 (1973).
Monod et al., Infection and Immunity, vol. 61, No. 10, pp. 4099–4104 (1993).
Rypniewski et al., Protein Engineering, vol. 6, No. 4, pp. 341–348 (1993).
J. R. Vasquez et al. J. Cell. Biochem. 39:265–276 (1989).

*Primary Examiner*—Rebecca E. Prouty
*Attorney, Agent, or Firm*—Steve T. Zelson; Cheryl H. Agris

[57] ABSTRACT

The present invention is related to a process for producing an active enzyme comprising fermenting the proform of the active enzyme in the present of a proteolytic enzyme different from the active enzyme and capable of converting the proenzyme into an active enzyme as well as to host cells, recombinant expression vectors and host cells suitable for use in the process.

28 Claims, 9 Drawing Sheets

```
       9        18       27       36       45       54
> ─── ─── ─── ─── ─── ─── ─── ─── ─── ─── ─── ─── ─── ─── ───
  ATG CGT TTC TCC GAC TCT CTC CTC CTC ATC GGC CTA TCC AGC CTC GCT GGT GCT
   M   R   F   S   D   S   L   L   L   I   G   L   S   S   L   A   G   A 63       72       81       90       99      108
  ─── ─── ─── ─── ─── ─── ─── ─── ─── ─── ─── ─── ───
  CAT CCC AGC AGA AGG GCT CCT AAT CCT TCA CCG CTG AGC AAG CGT GGC CTC GAC
   H   P   S   R   R   A   P   N   P   S   P   L   S   K   R   G   L   D 117      126      135      144      153      162
  ─── ─── ─── ─── ─── ─── ─── ─── ─── ─── ─── ─── ───
  CTG GAA GCT TTT AAG CTT CCT CCC ATG GCC GAG TAC GTT CCT CAG GAC GAG GTT
   L   E   A   F   K   L   P   P   M   A   E   Y   V   P   Q   D   E   V 171      180      189      198      207      216
  ─── ─── ─── ─── ─── ─── ─── ─── ─── ─── ─── ─── ───
  CCT GAT GAT GTC AGT GCC AAG GTC GTC ACC AAG CGC GCT GAT TAC ACC GAG ACT
   P   D   D   V   S   A   K   V   V   T   K   R   A   D   Y   T   E   T 225      234      243      252      261      270
  ─── ─── ─── ─── ─── ─── ─── ─── ─── ─── ─── ─── ───
  GCC AAG GAC TTG GTT AAG TCG ACT TTC CCC AAG GCT ACT TTC CGT ATG GTC ACG
   A   K   D   L   V   K   S   T   F   P   K   A   T   F   R   M   V   T 279      288      297      306      315      324
  ─── ─── ─── ─── ─── ─── ─── ─── ─── ─── ─── ─── ───
  GAT CAC TAT GTT GGT AGC AAC GGA ATT GCG CAT GTA AAC TTT AAG CAG ACT GTC
   D   H   Y   V   G   S   N   G   I   A   H   V   N   F   K   Q   T   V 333      342      351      360      373      383
  ─── ─── ─── ─── ─── ─── ─── ─── ─── ─── ─── ─── ───
  AAC GGT ATT GAT ATC GAC AAT GCT GAT TTC AAC GTC AAC GTGGGTATTC TCAAGACTTT
   N   G   I   D   I   D   N   A   D   F   N   V   N 393      403      413      424      433      442
                                        ─── ─── ─── ─── ─── ─── ───
  GGGGAGTTTG GAATGTGCTG ACATGGATAC AG ATT GGC GCT GAC GGC GAG GTC TTC TCC
                                         I   G   A   D   G   E   V   F   S 451      460      469      478      487      496
  ─── ─── ─── ─── ─── ─── ─── ─── ─── ─── ─── ─── ───
  TAC GGA AAC AGC TTC TAC GAG GGC AAG ATT CCC GGT CCT CTT ACC AAG CGT GAC
   Y   G   N   S   F   Y   E   G   K   I   P   G   P   L   T   K   R   D
```

FIG.3A

```
       505         514         523         532         541         550
       ___         ___         ___         ___         ___         ___
GAG AAA GAC CCC GTC GAC GCT CTC AAG GAC ACC GTT GAT GTT CTT TCT CTC CCC
 E   K   D   P   V   D   A   L   K   D   T   V   D   V   L   S   L   P 559         568         577         586         595         604
             ___         ___         ___         ___         ___         ___
GTT GAG GCT GAC AAG GCC AAG GCT GAG AAG AAG AGC AAG AAC CAC TAC ACC TTC
 V   E   A   D   K   A   K   A   E   K   K   S   K   N   H   Y   T   F 613         622         631         640         649         658
       ___         ___         ___         ___         ___         ___
ACT GGT ACC AAG GGT ACC GTC AGC AAG CCC GAG GCT AAG CTC ACC TAC CTT GTT
 T   G   T   K   G   T   V   S   K   P   E   A   K   L   T   Y   L   V 667         676         685         694         703         712
       ___         ___         ___         ___         ___         ___
GAT GAG AAC AAG GAG CTC AAG CTC ACA TGG AGA GTT GAG ACT GAT ATT GTT GAC
 D   E   N   K   E   L   K   L   T   W   R   V   E   T   D   I   V   D 721         730         739         748         757         766
       ___         ___         ___         ___         ___         ___
AAC TGG CTG TTG ACT TAT GTC AAT GCT GCC AAG ACT GAT GAG GTT GTT GGT GTT
 N   W   L   L   T   Y   V   N   A   A   K   T   D   E   V   V   G   V 775         784         793                     811         821
       ___         ___         ___                     ___         ___
GTT GAC TAC GTC AAT GAG GCG ACA TAC AAG GTC TA GTACGTATTT CCATAAATTG
 V   D   Y   V   N   E   A   T   Y   K   V   Y 831         841         851         861         870         879
                                           ___         ___         ___
ACGATTGGGA AAGAATTGAC CGTTGTATTA TAG T CCT TGG GGT GTC AAT GAT CCC TCC
                                     P   W   G   V   N   D   P   S 888         897         906         915         924         933
       ___         ___         ___         ___         ___         ___
AAG GGA TCT CGC TCC ACT GTT GAG AAC CCC TGG AAT CTC GCG GCC TCC GAG TTC
 K   G   S   R   S   T   V   E   N   P   W   N   L   A   A   S   E   F 942         951         960         969         978         987
       ___         ___         ___         ___         ___         ___
ACC TGG CTC AGC GAC GGC TCA AAC AAC TAC ACC ACA ACC CGC GGG AAC AAT GGA
 T   W   L   S   D   G   S   N   N   Y   T   T   T   R   G   N   N   G 996        1005        1014        1023        1032        1041
       ___         ___         ___         ___         ___         ___
ATT GCA CAG GTG AAT CCT TCA GGG GGC TCC ACG TAT CTG AAC AAT TAC CGT CCT
 I   A   Q   V   N   P   S   G   G   S   T   Y   L   N   N   Y   R   P
```

FIG.3B

|  | 1050 |  | 1059 |  | 1068 |  | 1077 |  | 1086 |  | 1095 |  |
|---|---|---|---|---|---|---|---|---|---|---|---|---|
| GAT | AGC | CCG | TCG | CTG | AAG | TTC | GAG | TAT | GAT | TAC | TCC | ACC | AGC | ACC | ACT | ACA | CCC |
| D | S | P | S | L | K | F | E | Y | D | Y | S | T | S | T | T | T | P |

|  | 1104 |  | 1113 |  | 1122 |  | 1131 |  | 1140 |  | 1149 |
|---|---|---|---|---|---|---|---|---|---|---|---|
| ACC | ACC | TAC | CGC | GAT | GCT | TCC | ATC | GCT | CAG | CTT | TTC | TAC | ACA | GCC | AAC | AAG | TAC |
| T | T | Y | R | D | A | S | I | A | Q | L | F | Y | T | A | N | K | Y |

|  | 1158 |  | 1167 |  | 1176 |  | 1185 |  | 1194 |  | 1203 |
|---|---|---|---|---|---|---|---|---|---|---|---|
| CAC | GAC | CTC | CTC | TAC | CTT | CTT | GGC | TTT | ACC | GAA | CAG | GCT | GGT | AAC | TTC | CAG | ACC |
| H | D | L | L | Y | L | L | G | F | T | E | Q | A | G | N | F | Q | T |

|  | 1212 |  | 1221 |  | 1230 |  | 1239 |  | 1248 |  | 1257 |
|---|---|---|---|---|---|---|---|---|---|---|---|
| AAC | AAC | AAT | GGC | CAG | GGT | GGT | GTA | GGA | AAC | GAT | ATG | GTT | ATC | CTC | AAC | GCT | CAG |
| N | N | N | G | Q | G | G | V | G | N | D | M | V | I | L | N | A | Q |

|  | 1266 |  | 1275 |  | 1284 |  | 1293 |  | 1302 |  | 1311 |
|---|---|---|---|---|---|---|---|---|---|---|---|
| GAC | GGA | AGC | GGC | ACC | AAC | AAC | GCC | AAC | TTC | GCT | ACA | CCC | GCT | GAC | GGT | CAG | CCC |
| D | G | S | G | T | N | N | A | N | F | A | T | P | A | D | G | Q | P |

|  | 1320 |  | 1329 |  | 1338 |  | 1347 |  | 1356 |  | 1365 |
|---|---|---|---|---|---|---|---|---|---|---|---|
| GGC | CGC | ATG | CGA | ATG | TAT | CTC | TGG | ACA | TAC | AGC | ACA | CCC | CAG | CGT | GAC | TGC | AGT |
| G | R | M | R | M | Y | L | W | T | Y | S | T | P | Q | R | D | C | S |

|  | 1374 |  | 1383 |  | 1392 |  | 1401 |  | 1410 |  | 1419 |
|---|---|---|---|---|---|---|---|---|---|---|---|
| TTC | GAC | GCT | GGC | GTT | GTT | ATC | CAC | GAG | TAC | ACT | CAC | GGT | CTC | TCC | AAC | CGT | CTC |
| F | D | A | G | V | V | I | H | E | Y | T | H | G | L | S | N | R | L |

|  | 1428 |  | 1437 |  | 1446 |  | 1455 |  | 1464 |  | 1473 |
|---|---|---|---|---|---|---|---|---|---|---|---|
| ACA | GGT | GGC | CCT | GCC | AAC | TCG | GGT | TGT | CTT | CCC | GGT | GGT | GAA | TCC | GGT | GGC | ATG |
| T | G | G | P | A | N | S | G | C | L | P | G | G | E | S | G | G | M |

|  | 1482 |  | 1491 |  | 1500 |  | 1509 |  | 1518 |  | 1527 |
|---|---|---|---|---|---|---|---|---|---|---|---|
| GGT | GAG | GGC | TGG | GGT | GAC | TTC | ATG | GCT | ACT | GCC | ATT | CAC | ATC | CCA | TCC | AAG | GAT |
| G | E | G | W | G | D | F | M | A | T | A | I | H | I | Q | S | K | D |

|  | 1536 |  | 1545 |  | 1554 |  | 1563 |  | 1572 |  | 1581 |
|---|---|---|---|---|---|---|---|---|---|---|---|
| ACC | CGC | GCT | AGC | AAC | AAG | GTC | ATG | GGT | GAC | TGG | GTG | TAC | AAC | AAC | GCA | GCT | GGT |
| T | R | A | S | N | K | V | M | G | D | W | V | Y | N | N | A | A | G |

FIG. 3C

```
      1590       1599       1608       1617       1626       1635
     ATC CGA GCT TAT CCT TAC AGT ACA AGC CTT ACC ACT AAC CCT TAC ACT TAC AAG
      I   R   A   Y   P   Y   S   T   S   L   T   T   N   P   Y   T   Y   K 1644       1653       1662       1671       1680       1689
     AGT GTT AAC AGT CTC AGT GGA GTC CAT GCT ATT GGT ACT TAC TGG GCT ACT GTT
      S   V   N   S   L   S   G   V   H   A   I   G   T   Y   W   A   T   V 1698       1707       1716       1725       1734       1743
     CTG TAT GAG GTT ATG TGG AAC CTC ATC GAC AAG CAT GGG AAG AAT GAT GCG GAT
      L   Y   E   V   M   W   N   L   I   D   K   H   G   K   N   D   A   D 1752       1761       1770       1779       1788       1797
     GAG CCC AAA TTC AAC AAC GGC GTT CCT ACA GAT GGC AAA TAT CTT GCT ATG AAG
      E   P   K   F   N   N   G   V   P   T   D   G   K   Y   L   A   M   K 1806       1815           1830       1840       1850
     1860
     TTA GTA GTG GAT GGC ATG TCG CT GTAAGTTGTC CCTTGGATTT GTAGGAGTTC
     TTATCTAACG
      L   V   V   D   G   M   S   L 1872       1881       1890       1899       1908
     TTTAATAG G CAA CCT TGC AAC CCC AAC ATG GTC CAG GCC CGA GAC GCC ATC ATC
                Q   P   C   N   P   N   M   V   Q   A   R   D   A   I   I 1917       1926       1935       1944       1953       1962
     GAC GCC GAC ACC GCT CTT ACC AAG GGA GCT AAC AAG TGC GAG ATC TGG AAG GGC
      D   A   D   T   A   L   T   K   G   A   N   K   C   E   I   W   K   G 1971       1980       1989       1998       2007       2016
     TTT GCC AAG CGT GGT CTT GGA ACT GGT GCC AAG TAT AGT GCT TCC AGC CGT ACT
      F   A   K   R   G   L   G   T   G   A   K   Y   S   A   S   S   R   T 2025       2034       2043       2052
                                          ⟶
     GAG AGC TTT GCT CTT CCT TCT GGA TGT TAA
      E   S   F   A   L   P   S   G   C
```

FIG.3D

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
  ( A ) LENGTH: 998 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:1:

```
ATCATCAACC ACTCTTCACT CTTCAACTCT CCTCTCTTGG ATATCTATCT CTTCACCATG     60
GTCAAGTTCG CTTCCGTCGT TGCACTTGTT GCTCCCCTGG CTGCTGCCGC TCCTCAGGAG    120
ATCCCCAACA TTGTTGGTGG CACTTCTGCC AGCGCTGGCG ACTTTCCCTT CATCGTGAGC    180
ATTAGCCGCA ACGGTGGCCC CTGGTGTGGA GGTTCTCTCC TCAACGCCAA CACCGTCTTG    240
ACTGCTGCCC ACTGCGTTTC CGGATACGCT CAGAGCGGTT TCCAGATTCG TGCTGGCAGT    300
CTGTCTCGCA CTTCTGGTGG TATTACCTCC TCGCTTTCCT CCGTCAGAGT TCACCCTAGC    360
TACAGCGGAA ACAACAACGA TCTTGCTATT CTGAAGCTCT CTACTTCCAT CCCCTCCGGC    420
GGAAACATCG GCTATGCTCG CCTGGCTGCT TCCGGCTCTG ACCCTGTCGC TGGATCTTCT    480
GCCACTGTTG CTGGCTGGGG CGCTACCTCT GAGGGCGGCA GCTCTACTCC CGTCAACCTT    540
CTGAAGGTTA CTGTCCCTAT CGTCTCTCGT GCTACCTGCC GAGCTCAGTA CGGCACCTCC    600
GCCATCACCA ACCAGATGTT CTGTGCTGGT GTTTCTTCCG GTGGCAAGGA CTCTTGCCAG    660
GGTGACAGCG GCGGCCCCAT CGTCGACAGC TCCAACACTC TTATCGGTGC TGTCTCTTGG    720
GGTAACGGAT GTGCCCGACC CAACTACTCT GGTGTCTATG CCAGCGTTGG TGCTCTCCGC    780
TCTTTCATTG ACACCTATGC TTAAATACCT TGTTGGAAGC GTCGAGATGT TCCTTGAATA    840
TTCTCTAGCT TGAGTCTTGG ATACGAAACC TGTTTGAGAA ATAGGTTTCA ACGAGTTAAG    900
AAGATATGAG TTGATTTCAG TTGGATCTTA GTCCTGGTTG CTCGTAATAG AGCAATCTAG    960
ATAGCCCAAA TTGAATATGA AATTTGATGA AAATATTC                           998
```

(2) INFORMATION FOR SEQ ID NO:2:

(i) SEQUENCE CHARACTERISTICS:
        (A) LENGTH: 248 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION: 25..248

(ix) FEATURE:
        (A) NAME/KEY: Peptide
        (B) LOCATION: 1..24

(xi) SEQUENCE DESCRIPTION: SEQ ID NO:2:

```
Met Val Lys Phe Ala Ser Val Val Ala Leu Val Ala Pro Leu Ala Ala
            -20              -15             -10
Ala Ala Pro Gln Glu Ile Pro Asn Ile Val Gly Gly Thr Ser Ala Ser
             -5               1               5
Ala Gly Asp Phe Pro Phe Ile Val Ser Ile Ser Arg Asn Gly Gly Pro
         10              15              20
Trp Cys Gly Gly Ser Leu Leu Asn Ala Asn Thr Val Leu Thr Ala Ala
 25              30              35                          40
His Cys Val Ser Gly Tyr Ala Gln Ser Gly Phe Gln Ile Arg Ala Gly
                 45              50                      55
Ser Leu Ser Arg Thr Ser Gly Gly Ile Thr Ser Ser Leu Ser Ser Val
             60              65              70
Arg Val His Pro Ser Tyr Ser Gly Asn Asn Asn Asp Leu Ala Ile Leu
     75              80                      85
Lys Leu Ser Thr Ser Ile Pro Ser Gly Gly Asn Ile Gly Tyr Ala Arg
 90              95              100
Leu Ala Ala Ser Gly Ser Asp Pro Val Ala Gly Ser Ser Ala Thr Val
105             110             115                         120
Ala Gly Trp Gly Ala Thr Ser Glu Gly Gly Ser Ser Thr Pro Val Asn
             125             130                     135
Leu Leu Lys Val Thr Val Pro Ile Val Ser Arg Ala Thr Cys Arg Ala
             140             145             150
Gln Tyr Gly Thr Ser Ala Ile Thr Asn Gln Met Phe Cys Ala Gly Val
         155             160             165
Ser Ser Gly Gly Lys Asp Ser Cys Gln Gly Asp Ser Gly Gly Pro Ile
     170             175             180
Val Asp Ser Ser Asn Thr Leu Ile Gly Ala Val Ser Trp Gly Asn Gly
 185             190             195             200
Cys Ala Arg Pro Asn Tyr Ser Gly Val Tyr Ala Ser Val Gly Ala Leu
             205             210                     215
Arg Ser Phe Ile Asp Thr Tyr Ala
             220
```

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
           Ala  Thr  Tyr  Lys  Val  Tyr  Pro  Trp  Gly  Val  Asn  Asp  Pro  Ser
           1                 5                      10
```

( 2 ) INFORMATION FOR SEQ ID NO:4:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
           Thr  Ala  Tyr  Ala  Ala  Arg  Gly  Thr  Ile  Thr  Ala  Tyr  Cys  Cys  Ile  Thr
           1                 5                      10                      15

Gly  Gly  Gly  Gly  Ile  Gly  Thr  Ile  Ala  Ala  Tyr  Gly  Ala  Tyr  Cys  Cys
                          20                      25                      30
```

( 2 ) INFORMATION FOR SEQ ID NO:5:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
           Gly  Thr  Tyr  Gly  Gly  Ile  Gly  Gly  Ile  Thr  Thr  Arg  Gly  Gly  Ile  Thr
           1                 5                      10                      15

Thr  Arg  Thr  Ala  Cys  Cys  Ala  Ile  Gly  Thr  Tyr  Cys  Gly
                          20                      25
```

( 2 ) INFORMATION FOR SEQ ID NO:6:

( i ) SEQUENCE CHARACTERISTICS:
        ( A ) LENGTH: 2052 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(1..363, 416..802, 856..1821, 1870..2052)

( i x ) FEATURE:
        ( A ) NAME/KEY: mat_peptide
        ( B ) LOCATION: join(1..363, 416..802, 856..1821, 1870..2049)

( x i ) SEQUENCE DESCRIPTION: SEQ ID NO:6:

```
ATG  CGT  TTC  TCC  GAC  TCT  CTC  CTC  CTC  ATC  GGC  CTA  TCC  AGC  CTC  GCT        48
Met  Arg  Phe  Ser  Asp  Ser  Leu  Leu  Leu  Ile  Gly  Leu  Ser  Ser  Leu  Ala
1                  5                        10                       15

GGT  GCT  CAT  CCC  AGC  AGA  AGG  GCT  CCT  AAT  CCT  TCA  CCG  CTG  AGC  AAG        96
Gly  Ala  His  Pro  Ser  Arg  Arg  Ala  Pro  Asn  Pro  Ser  Pro  Leu  Ser  Lys
                   20                       25                       30

CGT  GGC  CTC  GAC  CTG  GAA  GCT  TTT  AAG  CTT  CCT  CCC  ATG  GCC  GAG  TAC       144
Arg  Gly  Leu  Asp  Leu  Glu  Ala  Phe  Lys  Leu  Pro  Pro  Met  Ala  Glu  Tyr
              35                       40                       45

GTT  CCT  CAG  GAC  GAG  GTT  CCT  GAT  GAT  GTC  AGT  GCC  AAG  GTC  GTC  ACC       192
Val  Pro  Gln  Asp  Glu  Val  Pro  Asp  Asp  Val  Ser  Ala  Lys  Val  Val  Thr
     50                       55                       60

AAG  CGC  GCT  GAT  TAC  ACC  GAG  ACT  GCC  AAG  GAC  TTG  GTT  AAG  TCG  ACT       240
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Lys | Arg | Ala | Asp | Tyr | Thr | Glu | Thr | Ala | Lys | Asp | Leu | Val | Lys | Ser | Thr |     |
| 65  |     |     |     |     | 70  |     |     |     |     | 75  |     |     |     |     | 80  |     |
| TTC | CCC | AAG | GCT | ACT | TTC | CGT | ATG | GTC | ACG | GAT | CAC | TAT | GTT | GGT | AGC | 288 |
| Phe | Pro | Lys | Ala | Thr | Phe | Arg | Met | Val | Thr | Asp | His | Tyr | Val | Gly | Ser |     |
|     |     |     |     |     | 85  |     |     |     |     | 90  |     |     |     |     | 95  |     |
| AAC | GGA | ATT | GCG | CAT | GTA | AAC | TTT | AAG | CAG | ACT | GTC | AAC | GGT | ATT | GAT | 336 |
| Asn | Gly | Ile | Ala | His | Val | Asn | Phe | Lys | Gln | Thr | Val | Asn | Gly | Ile | Asp |     |
|     |     |     |     | 100 |     |     |     |     | 105 |     |     |     |     | 110 |     |     |
| ATC | GAC | AAT | GCT | GAT | TTC | AAC | GTC | AAC | GTGGGTATTC TCAAGACTTT |     |     |     |     |     | 383 |
| Ile | Asp | Asn | Ala | Asp | Phe | Asn | Val | Asn |     |     |     |     |     |     |     |     |
|     |     |     | 115 |     |     |     |     | 120 |     |     |     |     |     |     |     |     |

GGGGAGTTTG GAATGTGCTG ACATGGATAC AG ATT GGC GCT GAC GGC GAG GTC    436
                                                                              Ile Gly Ala Asp Gly Glu Val
                                                                                  125

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| TTC | TCC | TAC | GGA | AAC | AGC | TTC | TAC | GAG | GGC | AAG | ATT | CCC | GGT | CCT | CTT | 484  |
| Phe | Ser | Tyr | Gly | Asn | Ser | Phe | Tyr | Glu | Gly | Lys | Ile | Pro | Gly | Pro | Leu |      |
|     |     |     | 130 |     |     |     |     | 135 |     |     |     |     | 140 |     |     |      |
| ACC | AAG | CGT | GAC | GAG | AAA | GAC | CCC | GTC | GAC | GCT | CTC | AAG | GAC | ACC | GTT | 532  |
| Thr | Lys | Arg | Asp | Glu | Lys | Asp | Pro | Val | Asp | Ala | Leu | Lys | Asp | Thr | Val |      |
| 145 |     |     |     |     | 150 |     |     |     |     | 155 |     |     |     |     | 160 |      |
| GAT | GTT | CTT | TCT | CTC | CCC | GTT | GAG | GCT | GAC | AAG | GCC | AAG | GCT | GAG | AAG | 580  |
| Asp | Val | Leu | Ser | Leu | Pro | Val | Glu | Ala | Asp | Lys | Ala | Lys | Ala | Glu | Lys |      |
|     |     |     |     | 165 |     |     |     |     | 170 |     |     |     |     | 175 |     |      |
| AAG | AGC | AAG | AAC | CAC | TAC | ACC | TTC | ACT | GGT | ACC | AAG | GGT | ACC | GTC | AGC | 628  |
| Lys | Ser | Lys | Asn | His | Tyr | Thr | Phe | Thr | Gly | Thr | Lys | Gly | Thr | Val | Ser |      |
|     |     |     | 180 |     |     |     |     | 185 |     |     |     |     | 190 |     |     |      |
| AAG | CCC | GAG | GCT | AAG | CTC | ACC | TAC | CTT | GTT | GAT | GAG | AAC | AAG | GAG | CTC | 676  |
| Lys | Pro | Glu | Ala | Lys | Leu | Thr | Tyr | Leu | Val | Asp | Glu | Asn | Lys | Glu | Leu |      |
|     |     | 195 |     |     |     |     | 200 |     |     |     |     | 205 |     |     |     |      |
| AAG | CTC | ACA | TGG | AGA | GTT | GAG | ACT | GAT | ATT | GTT | GAC | AAC | TGG | CTG | TTG | 724  |
| Lys | Leu | Thr | Trp | Arg | Val | Glu | Thr | Asp | Ile | Val | Asp | Asn | Trp | Leu | Leu |      |
| 210 |     |     |     |     | 215 |     |     |     |     | 220 |     |     |     |     |     |      |
| ACT | TAT | GTC | AAT | GCT | GCC | AAG | ACT | GAT | GAG | GTT | GTT | GGT | GTT | GTT | GAC | 772  |
| Thr | Tyr | Val | Asn | Ala | Ala | Lys | Thr | Asp | Glu | Val | Val | Gly | Val | Val | Asp |      |
| 225 |     |     |     | 230 |     |     |     |     | 235 |     |     |     |     | 240 |     |      |
| TAC | GTC | AAT | GAG | GCG | ACA | TAC | AAG | GTC | TAT | GTACGTATTT CCATAAATTG |     |     |     |     | 822  |
| Tyr | Val | Asn | Glu | Ala | Thr | Tyr | Lys | Val | Tyr |     |     |     |     |     |     |      |
|     |     |     |     | 245 |     |     |     |     | 250 |     |     |     |     |     |     |      |

ACGATTGGGA AAGAATTGAC CGTTGTATTA TAG CCT TGG GGT GTC AAT GAT CCC    876
                                                                                 Pro Trp Gly Val Asn Asp Pro
                                                                                          255

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| TCC | AAG | GGA | TCT | CGC | TCC | ACT | GTT | GAG | AAC | CCC | TGG | AAT | CTC | GCG | GCC | 924  |
| Ser | Lys | Gly | Ser | Arg | Ser | Thr | Val | Glu | Asn | Pro | Trp | Asn | Leu | Ala | Ala |      |
|     |     || 260 |     |     |     |     | 265 |     |     |     |     | 270 |     |     |     |      |
| TCC | GAG | TTC | ACC | TGG | CTC | AGC | GAC | GGC | TCA | AAC | AAC | TAC | ACC | ACA | ACC | 972  |
| Ser | Glu | Phe | Thr | Trp | Leu | Ser | Asp | Gly | Ser | Asn | Asn | Tyr | Thr | Thr | Thr |      |
| 275 |     |     |     |     | 280 |     |     |     |     | 285 |     |     |     |     |     |      |
| CGC | GGG | AAC | AAT | GGA | ATT | GCA | CAG | GTG | AAT | CCT | TCA | GGG | GGC | TCC | ACG | 1020 |
| Arg | Gly | Asn | Asn | Gly | Ile | Ala | Gln | Val | Asn | Pro | Ser | Gly | Gly | Ser | Thr |      |
| 290 |     |     |     |     | 295 |     |     |     |     | 300 |     |     |     |     | 305 |      |
| TAT | CTG | AAC | AAT | TAC | CGT | CCT | GAT | AGC | CCG | TCG | CTG | AAG | TTC | GAG | TAT | 1068 |
| Tyr | Leu | Asn | Asn | Tyr | Arg | Pro | Asp | Ser | Pro | Ser | Leu | Lys | Phe | Glu | Tyr |      |
|     |     |     | 310 |     |     |     |     | 315 |     |     |     |     | 320 |     |     |      |
| GAT | TAC | TCC | ACC | AGC | ACC | ACT | ACA | CCC | ACC | ACC | TAC | CGC | GAT | GCT | TCC | 1116 |
| Asp | Tyr | Ser | Thr | Ser | Thr | Thr | Thr | Pro | Thr | Thr | Tyr | Arg | Asp | Ala | Ser |      |
|     |     |     | 325 |     |     |     |     | 330 |     |     |     |     | 335 |     |     |      |
| ATC | GCT | CAG | CTT | TTC | TAC | ACA | GCC | AAC | AAG | TAC | CAC | GAC | CTC | CTC | TAC | 1164 |
| Ile | Ala | Gln | Leu | Phe | Tyr | Thr | Ala | Asn | Lys | Tyr | His | Asp | Leu | Leu | Tyr |      |
|     |     |     | 340 |     |     |     |     | 345 |     |     |     |     | 350 |     |     |      |
| CTT | CTT | GGC | TTT | ACC | GAA | CAG | GCT | GGT | AAC | TTC | CAG | ACC | AAC | AAC | AAT | 1212 |

-continued

```
Leu Leu Gly Phe Thr Glu Gln Ala Gly Asn Phe Gln Thr Asn Asn Asn
    355             360             365
GGC CAG GGT GGT GTA GGA AAC GAT ATG GTT ATC CTC AAC GCT CAG GAC   1260
Gly Gln Gly Gly Val Gly Asn Asp Met Val Ile Leu Asn Ala Gln Asp
370             375             380             385
GGA AGC GGC ACC AAC AAC GCC AAC TTC GCT ACA CCC GCT GAC GGT CAG   1308
Gly Ser Gly Thr Asn Asn Ala Asn Phe Ala Thr Pro Ala Asp Gly Gln
            390             395             400
CCC GGC CGC ATG CGA ATG TAT CTC TGG ACA TAC AGC ACA CCC CAG CGT   1356
Pro Gly Arg Met Arg Met Tyr Leu Trp Thr Tyr Ser Thr Pro Gln Arg
                405             410             415
GAC TGC AGT TTC GAC GCT GGC GTT GTT ATC CAC GAG TAC ACT CAC GGT   1404
Asp Cys Ser Phe Asp Ala Gly Val Val Ile His Glu Tyr Thr His Gly
        420             425             430
CTC TCC AAC CGT CTC ACA GGT GGC CCT GCC AAC TCG GGT TGT CTT CCC   1452
Leu Ser Asn Arg Leu Thr Gly Gly Pro Ala Asn Ser Gly Cys Leu Pro
    435             440             445
GGT GGT GAA TCC GGT GGC ATG GGT GAG GGC TGG GGT GAC TTC ATG GCT   1500
Gly Gly Glu Ser Gly Gly Met Gly Glu Gly Trp Gly Asp Phe Met Ala
450             455             460             465
ACT GCC ATT CAC ATC CAA TCC AAG GAT ACC CGC GCT AGC AAC AAG GTC   1548
Thr Ala Ile His Ile Gln Ser Lys Asp Thr Arg Ala Ser Asn Lys Val
            470             475             480
ATG GGT GAC TGG GTG TAC AAC AAC GCA GCT GGT ATC CGA GCT TAT CCT   1596
Met Gly Asp Trp Val Tyr Asn Asn Ala Ala Gly Ile Arg Ala Tyr Pro
                485             490             495
TAC AGT ACA AGC CTT ACC ACT AAC CCT TAC ACT TAC AAG AGT GTT AAC   1644
Tyr Ser Thr Ser Leu Thr Thr Asn Pro Tyr Thr Tyr Lys Ser Val Asn
        500             505             510
AGT CTC AGT GGA GTC CAT GCT ATT GGT ACT TAC TGG GCT ACT GTT CTG   1692
Ser Leu Ser Gly Val His Ala Ile Gly Thr Tyr Trp Ala Thr Val Leu
    515             520             525
TAT GAG GTT ATG TGG AAC CTC ATC GAC AAG CAT GGG AAG AAT GAT GCG   1740
Tyr Glu Val Met Trp Asn Leu Ile Asp Lys His Gly Lys Asn Asp Ala
530             535             540             545
GAT GAG CCC AAA TTC AAC AAC GGC GTT CCT ACA GAT GGC AAA TAT CTT   1788
Asp Glu Pro Lys Phe Asn Asn Gly Val Pro Thr Asp Gly Lys Tyr Leu
            550             555             560
GCT ATG AAG TTA GTA GTG GAT GGC ATG TCG CTG GTAAGTTGTC CCTTGGATTT 1841
Ala Met Lys Leu Val Val Asp Gly Met Ser Leu
            565             570
GTAGGAGTTC TTATCTAACG TTTAATAG CAA CCT TGC AAC CCC AAC ATG GTC    1893
                             Gln Pro Cys Asn Pro Asn Met Val
                                     575             580
CAG GCC CGA GAC GCC ATC ATC GAC GCC GAC ACC GCT CTT ACC AAG GGA   1941
Gln Ala Arg Asp Ala Ile Ile Asp Ala Asp Thr Ala Leu Thr Lys Gly
            585             590             595
GCT AAC AAG TGC GAG ATC TGG AAG GGC TTT GCC AAG CGT GGT CTT GGA   1989
Ala Asn Lys Cys Glu Ile Trp Lys Gly Phe Ala Lys Arg Gly Leu Gly
            600             605             610
ACT GGT GCC AAG TAT AGT GCT TCC AGC CGT ACT GAG AGC TTT GCT CTT   2037
Thr Gly Ala Lys Tyr Ser Ala Ser Ser Arg Thr Glu Ser Phe Ala Leu
            615             620             625
CCT TCT GGA TGT TAA                                               2052
Pro Ser Gly Cys
630
```

( 2 ) INFORMATION FOR SEQ ID NO:7:

( i ) SEQUENCE CHARACTERISTICS:
( A ) LENGTH: 36 base pairs

-continued

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGATCCTCGA ATTCTCTTCA GATCTCTTCA CCATGG                                  36

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGATCCACCA TGG                                                           13

(2) INFORMATION FOR SEQ ID NO:9:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Ala Asp Tyr Gln Val Tyr Ala Trp Gly Ile Asn Asp Pro Thr
    1               5                   10
```

PROCESSES FOR PRODUCING AN ENZYME

FIELD OF THE INVENTION

The present invention relates to processes for producing an enzyme, as well as to a cell and a DNA construct suitable for use in the processes. By use of the processes of the invention, it is possible to obtain substantially increased enzyme yields.

BACKGROUND OF THE INVENTION

Enzymes, which are protein molecules capable of catalyzing specific reactions, have been found useful for a number of applications within a wide range of industries and technical fields, including the detergent industry, the food and feed industry, the paper and pulp industry as well as the textile industry. Enzymes have a number of important advantages over chemical agents which conventionally have been used for same or similar purposes, one advantage being that they are readily degraded and thus, in general, less harmful to the environment than chemical agents. Accordingly, for a number of purposes enzymes are considered to be attractive substituents for chemical agents conventionally used.

Enzymes are normally produced by fermentation of microbial cells or cells of other organisms, which either inherently or as a consequence of being transformed with a nucleic acid sequence encoding the enzyme in question, are capable of producing the enzyme. A number of enzymes are expressed from the producer cell in the form of an inactive proenzyme, which upon expression is converted to an active enzyme, typically by being processed by the action of one or more proteolytic enzymes expressed by the producer cell. Processing by externally supplied activators has also been reported, e.g. the activation of bovine prochymosin by a fungal metalloprotease (Stepanov et al, 1990, Vol. 260, No. 2, pp. 173–175).

Although the development and use of recombinant DNA technology in the production of enzymes was a major break-through in respect of increasing the yield of specific enzymes, it is an ever existing wish to obtain further improvements as concerns yield, thereby, for instance, to be able to meet the still increasing demand for enzymes and to improve the economy of enzyme production.

BRIEF DISCLOSURE OF THE INVENTION

It has now surprisingly been found that it is possible to obtain substantial increases in the yield of an active enzyme produced as a proenzyme by fermentation of a cell capable of expressing the proenzyme, when a proteolytic enzyme is present in the broth in which the cell is fermented.

Accordingly, the present invention relates to a process for producing an active enzyme by fermentation of a cell expressing the enzyme in the form of a proenzyme, which process comprises performing the fermentation in the presence of a proteolytic enzyme capable of converting the proenzyme into an active enzyme, and recovering the active enzyme from the fermentation broth, the proteolytic enzyme being added to the fermentation broth prior to and/or during the fermentation.

In contrast to what would be expected from producing a protein in the presence of a proteolytic, i.e. protein-degrading, enzyme, the presence of a proteolytic enzyme has been found to result in a substantial increased enzyme yield, more specifically in an increase of more than 2 times, such as more than 4, and even more than 6 or 8 times of the amount of active enzyme produced by a given fermentation as compared to a process in which no proteolytic enzyme is added and in which the activation of the proenzyme thus typically is performed by a proteolytic enzyme expressed by the host cell in question.

In the present context the term "active enzyme" is intended to indicate a form of the enzyme exhibiting enzymatic activity, e.g. a mature enzyme. The enzymatic activity may be determined by assays known in the art for the enzyme in question.

The term "proenzyme" is intended to indicate a precursor or proform of the enzyme. Typically, the proenzyme is constituted by a propeptide part and a polypeptide part comprising the amino acid sequence of the active enzyme. The proenzyme may also be termed a zymogen or a precursor. The proenzyme may be stable in the fermentation broth or may be less stable than the active enzyme in the fermentation broth, in which it is produced, e.g. by being degraded more rapidly in the fermentation broth than the active enzyme.

The term "proteolytic enzyme" or "maturase" is used interchangeably in the instant application and is intended to indicate an enzyme capable of cleaving off the propeptide from the proenzyme expressed from the cell, whereby the "conversion" of the proenzyme into an active or mature enzyme is accomplished. Preferably, the proteolytic enzyme does not or only to a limited extent cleave peptide sequences of the active enzyme required for enzymatic activity. The proteolytic enzyme may be one which in nature cleaves the pro sequence from the proenzyme in question to produce the active enzyme, in which case a further amount is added in accordance with the invention, or may be different from the natural enzyme.

The term "fermentation" is intended to indicate any method of cultivation of the cell resulting in the expression of the enzyme in the form of a proenzyme. Thus, the fermentation may be understood as comprising shake flask cultivation, small or large scale fermentation (including continuous, batch and fed-batch fermentations) in laboratory or industrial fermenters etc. performed in suitable fermentation media and under conditions allowing the proenzyme to be expressed.

In a second aspect, the present invention relates to a process for producing an active enzyme by fermentation of a cell expressing the enzyme in the form of a proenzyme, which process comprises performing the fermentation in the presence of a proteolytic enzyme capable of converting the proenzyme into an active enzyme, and recovering the active enzyme from the fermentation broth, the proteolytic enzyme being encoded by and expressed from a recombinant DNA sequence present in the cell from which the proenzyme is expressed. It is contemplated that increases in the yield of an active enzyme similar to those obtained by the process explained above, may be obtained in accordance with this aspect of the invention. The process according to this second aspect has the important advantage that no proteolytic enzyme need to be added during the process, although it can be as it is further described below.

In the present context the term "recombinant DNA sequence" is intended to indicate a heterologous DNA sequence with which the cell expressing the proenzyme has been transformed. The term "heterologous" is intended to indicate that the cell expressing the proenzyme does not, in nature, comprise said DNA sequence encoding the proteolytic enzyme. Alternatively, the term "recombinant DNA sequence" is intended to indicate a DNA sequence which is normally found in the cell expressing the proenzyme, but which has been placed under the control of one or more regulatory elements, e.g. a promoter, different from the one(s) associated with the naturally-occurring DNA sequence and capable of increasing the amount of active proteolytic enzyme expressed from the DNA sequence. Furthermore, the term is intended to indicate a DNA construct in which the copy number of the DNA sequence encoding the proteolytic enzyme has been increased.

In a further aspect, the present invention relates to a host cell comprising a heterologous nucleic acid fragment containing a nucleic acid sequence encoding a proenzyme and a heterologous nucleic acid fragment containing a nucleic acid sequence encoding a proteolytic enzyme capable of converting the proenzyme into an active enzyme, the proenzyme being less stable than the active enzyme, in which host cell at least one of the nucleic acid sequences is a recombinant nucleic acid sequence.

In still further aspects, the present invention relates to a DNA construct comprising a DNA sequence encoding a proenzyme and a DNA sequence encoding a proteolytic enzyme capable of converting the proenzyme into an active enzyme, the proenzyme being less stable than the active enzyme.

The host cell, DNA construct and expression vector are advantageously used in a process of the invention and may be produced in accordance with conventional recombinant DNA techniques.

Finally, the present invention relates to an active enzyme produced by a process of the invention.

BRIEF DESCRIPTION OF THE DRAWINGS

The invention is further illustrated in the accompanying drawings, in which

FIGS. 3A–3D show the genomic DNA sequence and deduced amino acid sequence of p45 as determined from the sequencing of the cDNA.

FIG. 4 shows a map of plasmid pDM120.

FIG. 5 shows a map of plasmid pSO2.

FIG. 6 shows SDS-PAGE analysis of *A. oryzae* transformants containing both the pro *F. oxysporum* trypsin-like protease and the *F. oxysporum* p45 proteolytic enzyme genes. The lanes contain supernatants from: lane 1, molecular weight markers; lane 2, control *A. oryzae* strain (untransformed); lane 3, *A. oryzae* transformed with p45 only; lane 4, *A. oryzae* transformed with pSX183 trypsin-like protease only; lanes 5–10, *A. oryzae* strains transformed with both p45 and the pro *F. oxysporum* trypsin-like protease.

FIG. 7 shows a comparision of the N-terminal amino acid sequence of purified npI with p45.

DETAILED DISCLOSURE OF THE INVENTION

The proenzyme produced during the processes of the invention may be stable in the fermentation broth, i.e. not subjected to any substantial degradation, and thus be capable of being converted into an active enzyme over a considerable period of time while being present in or recovered from the fermentation broth. Alternatively, the proenzyme may be unstable and quickly degraded in the fermentation broth, in worst case before having been recovered or converted to an active enzyme. The processes of the invention are contemplated to be particularly important in the production of enzymes, in which the proenzyme form of which, in the fermentation broth, is less stable than the active enzyme. In such cases, it is believed that the proteolytic enzyme is capable of converting the unstable proenzyme into an active enzyme prior to the degradation thereof.

Although the processes of the invention may be advantageous for the production of active enzymes by fermentation of naturally-occurring cells expressing the corresponding proenzyme, they are envisaged to be of particular importance in the production of active recombinant enzymes, i.e. enzymes encoded by nucleic acid sequences which have been transformed into the cell subjected to fermentation.

Accordingly, it is preferred that the cell expressing the proenzyme has been transformed with a heterologous nucleic acid fragment containing a nucleic acid, e.g. DNA or RNA sequence, encoding the proenzyme. The transformation may be accomplished by conventional methods known in the art chosen so as to comply with the nature of the host cell of choice as well as of the nature of the nucleic acid sequence. The nucleic acid sequence may be inserted into the genome of the host cell, e.g. by homologous or heterologous recombination. Alternatively, the nucleic acid sequence may be inserted into a recombinant expression vector capable of autonomous replication in the host cell. Specifically, the nucleic acid fragment is operably linked to transcription and translation signals capable of directing expression of the proenzyme.

It is presently believed that the processes of the invention may be generally applicable for the production of any active enzyme which in the cell is expressed as a proenzyme, and in particular an enzyme, the corresponding proenzyme of which, in the fermentation broth, is less stable than the active enzyme. For instance, the enzyme to be produced by a process of the invention may be a hydrolase, an oxidoreductase, an isomerase, an oxidase or a transferase.

In particular, the enzyme to be produced may be a protease, a lipase, an amylase, a cellulase, a xylanase, a pectinase, a peroxidase, a laccase or a transglutaminase.

In the present context, the enzyme to be produced may be a naturally occurring enzyme or a genetically engineered variant thereof, in which one or more amino acid residues has been changed e.g. by conventional or site-directed mutagenesis.

One type of enzyme, for which an improved yield has been obtained by use of a process of the invention, is a trypsin-like protease.

In the present context the term "trypsin-like protease" is intended to indicate trypsin or an enzyme having a structure or an activity similar to that of trypsin, e.g. an enzyme capable of cleaving peptide bonds at the C-terminal side of lysine or arginine. The trypsin-like protease activity may be determined in an assay based on cleavage of a trypsin substrate such as N-Benzoyl-L-arginine-p-nitroanilide (L-BAPNA), e.g. as described in the Materials and Methods section below.

Trypsin-like proteases have been found to be produced by a number of difference organisms including mammals, insects and microorganisms. An example of a microorganism producing a trypsin-like protease is one of the fungal genus Fusarium, cf. U.S. Pat. No. 5,288,627, incorporated herein by reference and accordingly, the enzyme to be produced may be obtainable from a strain of the genus Fusarium, such as from a strain of *F. oxysporum, F. merismoides, F. redolens, F. sambucinum, F. solani* or *F. verticilloides*.

Figure 1:
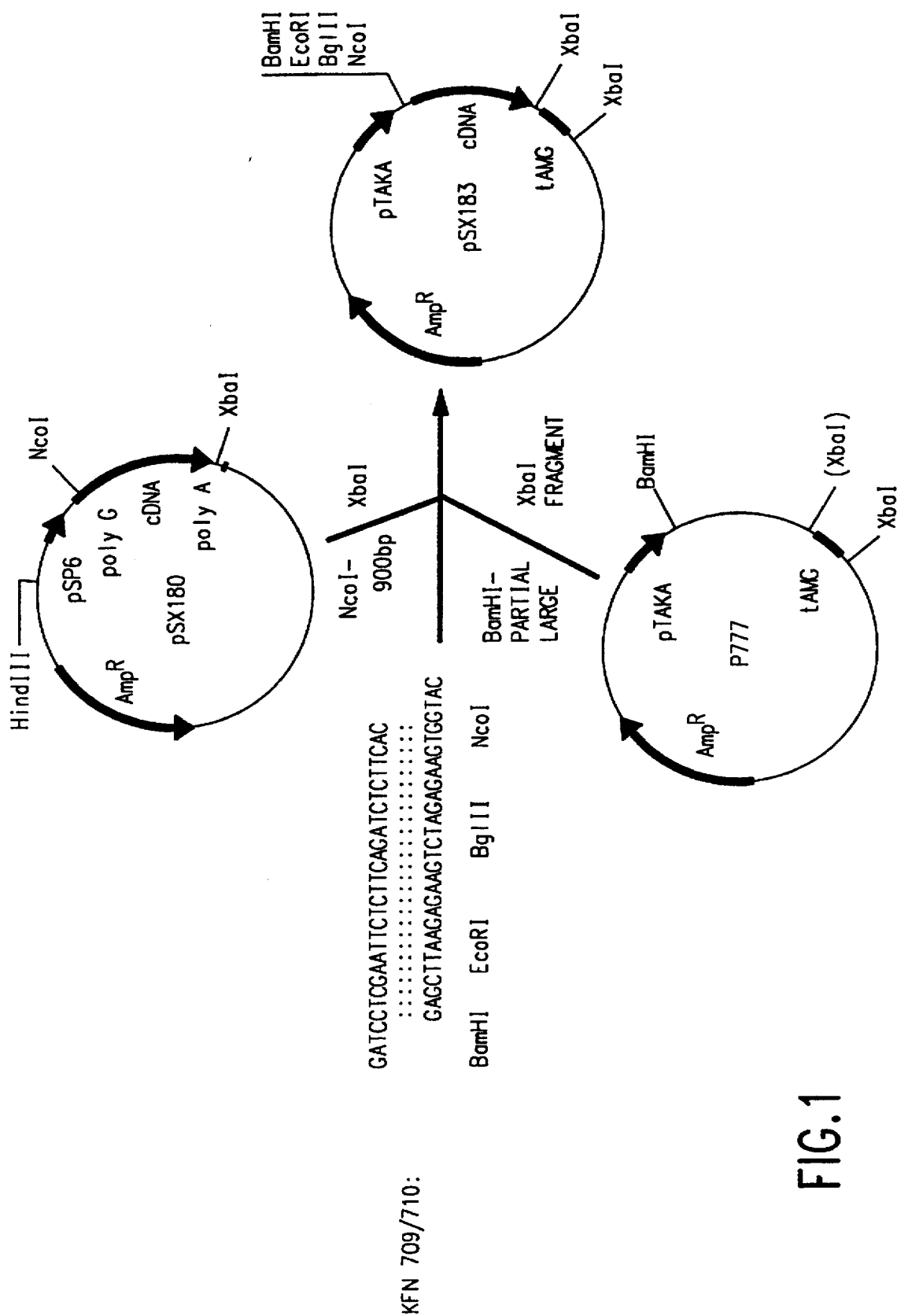
FIG. 1 illustrates the construction of the expression plasmid pSX183 used for the expression of a recombinant trypsin-like *F. oxysporum* protease further described in the accompanying examples.

In particular, the enzyme is one obtainable from a strain of *F. oxysporum*, e.g. a strain deposited in the Deutsche Sammlung yon Mikroorganismen in connection with the invention disclosed in U.S. Pat. No. 5,288,627 with the deposit number DSM 2672, or from a derivative or mutant thereof having retained the capability of producing an enzyme having an activity similar to that of trypsin as defined above. The nucleic acid sequence coding for and the amino acid sequence of the trypsin-like *F. oxysporum* protease isolated from this strain is illustrated in the appended SEQ ID NOS: 1 and 2, respectively.

The proenzyme produced by a process of the invention may be a preproenzyme, and thus carry a signal peptide involved in the transportation of the proenzyme out of the cell in which it is produced. The signal peptide may be one normally associated with the proenzyme in question or one, which has been fused to the proenzyme, e.g. in order to suit the excretion procedures of the host cell of choice for the expression of the proenzyme.

In accordance with the processes of the invention, the activation of the proenzyme is normally accomplished by one proteolytic enzyme although, for some purposes, it may be found advantageous to use a combination of two or more proteolytic enzymes having similar or different enzymatic activities.

The nature of the proteolytic enzyme(s) capable of converting the proenzyme into an active enzyme depends strongly on the nature of the proenzyme to be converted. Thus, the proteolytic enzyme(s) to be used for the activation of a specific enzyme may be chosen on the basis of an analysis of the peptide sequence to be cleaved.

When the amino acid sequence of the proenzyme or of the active enzyme is known or is deducible from a nucleic acid sequence known or contemplated to encode the enzyme, one may identify the propeptide in the sequence or a limited number of possible propeptides using well-known procedures, and thereby determine the peptide sequence to be cleaved. On the basis thereof, one or more proteolytic enzymes known to or contemplated to be capable of cleaving the particular peptide sequence(s) may then be identified, and the use thereof be verified experimentally. Of course, the proteolytic enzyme(s) of choice should not, or only to a limited extend, cleave peptide bonds present in the active enzyme thereby hindering a destruction or substantial reduction of the activity of the active enzyme produced by the process. Alternatively to the above procedure, one may identify one or more useful proteolytic enzymes experimentally.

From the above, it will be understood that a proteolytic enzyme to be used in a process of the invention may be any enzyme having a suitable proteolytic activity. For instance, the proteolytic enzyme may be a metalloprotease, a serine protease, an aspartic protease, a cysteine protease, whether of neutral, alkaline or acidic nature. The enzyme may be specific or unspecific. Examples of such proteolytic enzyme may be found among the proteinases belonging to the enzyme nomenclature classes 3.4.21–3.4.24 according to Enzyme Nomenclature, 1984.

For the activation of a trypsin-like protease, especially one produced by a Fusarium sp. such as *F. oxysporum*, a neutral metalloprotease, a subtilisin or an aspartic protease is expected to be of particular use. When the trypsin-like protease is the one produced by the *F. oxysporum* DSM 2672, the proteolytic enzymes thermolysin or a proteolytic enzyme from Bacillus (Zamost et al., 1990, Journal of Industrial Microbiology, Vol. 5, pp. 303–312), e.g. Bacillus metalloprotease preparation may be used. The proteolytic enzyme may also be a metalloprotease obtainable from *Aspergillus oryzae* or *Fusarium oxysporum* disclosed in Examples 4 and 6, infra. In one embodiment, the proteolytic enzyme may be used to increase the yield of the trypsin-like *F. oxysporum* protease when produced by *F. oxysporum*. In this case, the proteolytic enzyme is present in an excessive amount as compared to conventional fermentation.

From the above disclosure it will be apparent that the proteolytic enzyme(s) may be added as such to the fermentation broth in which the cell producing the proenzyme to be converted is cultured. The proteolytic enzyme may be added batchwise or continuously. The proteolytic enzyme(s) to be added may for instance be a commercially available enzyme, e.g. one of those mentioned above, or may be produced by culturing a host cell inherently carrying or being transformed with a nucleic acid sequence encoding the proteolytic enzyme under suitable conditions to produce the enzyme and recovering the enzyme from the culture.

Alternatively, the presence of the proteolytic enzyme(s) in the fermentation broth may be accomplished by constructing a cell capable of expressing the proenzyme and the proteolytic enzyme(s), and cultivating the cell under conditions conducive to the production of the proenzyme and the proteolytic enzyme(s) and to the subsequent activation of the proenzyme by the proteolytic enzyme(s). A suitable cell may be constructed by being transformed with nucleic acid sequences encoding the proenzyme and the proteolytic enzyme(s), optionally present on one or more expression vectors. Alternatively, one may choose a cell already comprising a heterologous nucleic acid fragment containing a nucleic acid sequence encoding, for instance, the proenzyme and inserting a nucleic acid sequence encoding a proteolytic enzyme into said cell (or vice versa) by recombinant DNA methods.

In an alternative embodiment, the processes of the invention may be carried out by subjecting a cell expressing the proenzyme and a cell expressing a proteolytic enzyme capable of converting the proenzyme into an active form to co-expression under suitable conditions allowing the expression of said proenzyme and said proteolytic enzyme and the conversion of the proenzyme into an active enzyme, and recovering the active enzyme in from the culture. According to this embodiment it is preferred that at least one of said proenzyme and proteolytic enzyme is recombinant.

In accordance with the present invention, the proteolytic enzyme should be present in a sufficient amount for the activation of the proenzyme to take place. The amount of proteolytic enzyme to be present may be determined by model experiments in accordance with methods known in the art. For instance, the determination of a suitable amount may be based on estimations of $K_M$-values and rate constants for respectively the enzyme reactions degrading the proenzyme and the enzyme reaction converting the proenzyme into an active enzyme.

Alternatively, the amount of proteolytic enzyme necessary may be determined emperically by carrying out fermentations with dosing of proteolytic enzyme. The fermentation conditions, e.g. pH and temperature, should be optimal for stability of the proenzyme and stability and activity of the proteolytic enzyme.

If the proteolytic enzyme is expected to be easily degraded in the fermentation broth, for instance by the active enzyme produced according to a process of the invention, it may be advantageous to supply the enzyme continuously or in several portions, e.g. by use of a fed batch feeding.

When the proteolytic enzyme is expressed from the same cell as the proenzyme, it may be advantageous to add a further amount (in addition to that produced from the cell) of said proteolytic enzyme to the fermentation broth during the cultivation of the cell.

When coexpression is used, the maturation of the proenzyme may be accomplished intracellularly, provided that the thus mature or activated enzyme is not detrimental to the cell, and may be recovered from the cell in mature or active form.

It is presently believed that an additional positive effect on the yield of an active enzyme produced by a process of the invention may be obtained by stabilizing the proenzyme, especially when the proenzyme is unstable in the fermentation broth. For instance, such stabilization may result in a higher intracellular stability of the proenzyme and thus a higher amount of proenzyme available for the activation by the proteolytic enzyme. The stabilization may be performed by suitably modifying the nucleic acid sequence coding for the propeptide part of the proenzyme in accordance with well-known procedures, resulting in the addition of one or more amino acids to either or both the C- and N-terminal end of the propeptide, substitution of one or more amino acids at one or a number of different sites in the amino acid sequence of the propeptide, deletion of one or more amino acids at either or both ends of the propeptide or at one or more sites in the amino acid sequence, or insertion of one or more amino acids at one or more sites in the amino acid sequence of the propeptide, so as to obtain a higher stability of the proenzyme.

Alternatively, a stabilizing effect may be obtained by constructing a fusion protein comprising the proenzyme or a part thereof capable of being converted into a active or mature protein having enzymatic activity and a stabilizing protein or part thereof.

The nucleic acid sequences encoding the proenzyme and/or the proteolytic enzyme(s) as well as the DNA construct of the invention may be of genomic or cDNA origin, for instance obtained by preparing a genomic or cDNA library of an appropriate organism, and screening for DNA sequences coding for all or part of the proenzyme or proteolytic enzyme by hybridization using synthetic oligonucleotide probes, e.g. prepared on the basis of the amino acid sequence of the proenzyme or proteolytic enzyme, in accordance with standard techniques (cf. Sambrook et al., Molecular Cloning: A Laboratory Manual, 2nd Ed., Cold Spring Harbor, 1989).

The DNA sequences and the DNA construct of the invention may also be prepared synthetically by established standard methods, e.g. the phosphoamidite method described by S. L. Beaucage et al. (1981), Tetrahedron Letters 22, pp. 1859–1869 and Matthes et al. (1984), The EMBO J. 3: 801–805. According to the phosphoamidite method, oligonucleotides are synthesized, e.g. in an automatic DNA synthesizer, purified, ligated, and cloned in an appropriate vector.

Finally, the DNA sequences and the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques.

The cell used for the expression of the proenzyme and/or the proteolytic enzyme(s) in processes of the invention is suitably a cell which, on cultivation, produces large amounts of the proenzyme and/or the proteolytic enzyme(s). As stated above, the cell may be one which in nature produces the proenzyme or the proteolytic enzyme(s), but is preferably a cell of the invention which has been transformed with a nucleic acid sequence encoding the proenzyme and/or a nucleic acid sequence encoding the proteolytic enzyme(s). The cell may conveniently be one which has previously been used as a host for producing recombinant proteins, either a prokaryotic or eukaryotic cell, including but not limited to mammalian cells, insect cells, plant cells or fungal cells and is preferably a microorganism such as a bacterium or a fungus. The term "fungus" is intended to comprise filamentous fungi as well as yeasts.

Examples of suitable bacteria are gram positive bacteria of the genus Bacillus such as *Bacillus subtills, Bacillus licheniformis, Bacillus lentus, Bacillus brevis, Bacillus stearothermophilus, Bacillus alkalophilus, Bacillus amyloliquefaciens, Bacillus coagulans, Bacillus megaterium, Bacillus circulans, Bacillus lautus* and of the genus Streptomyces such as *Streptomyces lividans*. Examples of suitable gram-negative bacteria comprises bacteria of the genus Escherichia such as *E. coli*. The transformation of the bacterial host cell may for instance be effected by protoplast transformation or by using competent cells in a manner known per se. Another suitable bacterial cell is a cell of a Pseudomonas spp. such as *Pseudomonas cepacia, Pseudomonas fragi, Pseudomonas gladioli, Pseudomonas fluorescens, Pseudomonas stutzeri, Pseudomonas alcaligenes, Pseudomonas pseudoalcaligenes, Pseudomonas putida, Pseudomonas glumae* or *Pseudomonas aeruginosa*.

Alternatively, the cell may be a fungus, i.e. a cell of a yeast or of a filamentous fungus. The yeast cell may, for instance, be a cell of the genus Saccharomyces such as *S. cerevisiae*. The filamentous fungus host organism may, for instance, be a strain of Aspergillus sp., such as *A. niger, A. nidulans* or *A. oryzae*. The techniques used to transform an Aspergillus host cell and obtain expression of the recombinant protein may suitably be as described in EP 238 023. Alternatively, the fungal host cell may be a strain of a Fusarium sp. such as *F. oxysporum*, the transformation of which, e.g., may be carried out as described by Malardier et al., 1989, Gene 78: 147–156.

In the host cell of the invention, the nucleic acid sequence encoding the proenzyme and/or the nucleic acid sequence encoding the proteolytic enzyme may be carried on an expression vector or alternatively be present in the genome of the host cell.

In order to obtain expression, the nucleic acid sequence encoding the proenzyme and/or proteolytic enzyme(s) are/is normally preceded by a promoter. The promoter may be any nucleic acid sequence exhibiting a strong transcriptional activity in the host cell of choice and may be derived from a gene encoding an extracellular or intracellular protein such as an amylase, a glucoamylase, a protease, a lipase, a cellulase or a glycolytic enzyme. Examples of suitable promoters, especially when using a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus Amyloliquefaciens* α-amylase (amyQ), the promoters of the *Bacillus subtilis* xylA and xinB genes, etc. For transcription in a fungal host, examples of useful promoters are those derived from the gene encoding *A. oryzae* TAKA amylase, *Rhizormcor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

Other sequences involved in expression of the proenzyme include termination and polyadenylation sequences as well as ribosome binding sites and may suitably be derived from the same sources as the promoter.

The vector may further comprise a nucleic acid sequence enabling the vector to replicate in the host cell in question, e.g. a suitable origin of replication, as well as a selectable marker, e.g. a gene the product of which complements a defect in the host cell, or one which confers antibiotic resistance to the host cell.

The procedures used to ligate the DNA construct of the invention, the promoter, terminator and other elements, respectively, and to insert them into suitable vectors containing the information necessary for replication, are well known to persons skilled in the an (cf., for instance, Sambrook et al., Molecular Cloning, Cold Spring Harbor, N.Y., 1989).

The cell of the invention either comprising a DNA construct or an expression vector of the invention as defined above is advantageously used as a host cell in the recombinant production of a enzyme of the invention. The cell may be transformed with the DNA construct of the invention, conveniently by integrating the DNA construct in the host chromosome. The resulting host cell is a "recombinant host cell". This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The broth or medium used in the processes of the invention for cultivation of the resulting recombinant host cell may be any conventional medium suitable for growing the cell in question. Suitable media, e.g. minimal or complex media, are available from commercial suppliers or may be prepared according to published recipes (e.g. in catalogs of the American Type Culture Collection).

The enzyme may be recovered from the broth by conventional procedures including separating the cells from the broth by centrifugation or filtration, if necessary after disruption of the cells, precipitating the proteinaceous components of the supernatant or filtrate by means of a salt, e.g. ammonium sulphate, followed by purification by a variety of chromatographic procedures, e.g. ion exchange chromatography, affinity chromatography, or the like, the actual recovery method being dependant on the kind of enzyme in question.

The present invention is further illustrated by the following examples which are not in any way intended to limit the scope of the invention as defined herein.

EXAMPLES

Example 1: Enzyme Activation In Shake Flask Fermentations

The effect of using different levels of *Bacillus stearothermophilus* (BS) protease on the yield of a trypsin-like Fusarium protease is evaluated by shake flask fermentation with minimal and complex media, respectively, at fermentation temperatures of 34° C., 30° C. and 26° C.

MATERIALS AND METHODS

Fungal strains

*Fusarium oxysporum* DSM 2672 deposited on 6 Jun. 1983 at Deutsche Sammlung yon Mikroorganismen, Göttingen, Germany, under the terms of the Budapest Treaty and further described in U.S. Pat. No. 5,288,627.

*Aspergillus oryzae* IFO 4177

Construction of a recombinant *A. oryzae* strain capable of expressing the trypsin-like *F. oxysporum* protease cDNA encoding a proenzyme form of the trypsin-like *F. oxysporum* protease and having the DNA sequence shown in the appended SEQ ID NO:1 is inserted into the vector pCDV1-PL described by Noma et al. (1986), Nature 319:640–646 resulting in the plasmid pSX 180. The coding region of the cDNA is inserted as a NcoI-XbaI fragment into the Aspergillus expression plasmid p777 (EP 0 489 718) which is cut with BamHI and partially with XbaI. To join the 5' end of the cloned DNA to the vector a synthetic linker DNA KFN709/710 (illustrated in FIG. 1) is added to the ligation reaction. The resulting plasmid pSX183 is co-transformed into *A. oryzae* (IFO 4177) together with plasmid pToC90 carrying the amdS from *A. nidulans* (WO 91/17243). Transformants are selected for growth on acetamide.

Proteolytic enzyme

The *Bacillus stearothermophilus* (BS) protease TPM-8 described by Zamost et al. (1990), Journal of Industrial Microbiology, Vol. 5, pp. 303–312 has been used. For shake flask fermentation in the form of a freeze-dried powder with an activity of 5.0 AU(H)/g, for model experiments (Example 2) in the form of crystalline BS-protease with 75 AU(H)/g. The specific activity of the enzyme is approx. 100 AU(H)/g.

Fermentation

| Complex medium: | FG4P medium | |
|---|---|---|
| | 15.0 g/l | Maltodextrin |
| | 30.0 g/l | Soy flour |
| | 5.0 g/l | Bacto peptone |
| | 15.0 g/l | $KH_2PO_4$ |
| | 0.4 g/l Pluronic ® | (BASF) pH 6.5 |
| Minimal medium: | ASP02 medium | |
| | Succinic acid | 10.0 g/l |
| | $MgCl_2$ 6 $H_2O$ | 0.8 g/l |
| | KCl | 1.8 g/l |
| | $NaH_2PO_4$ $H_2O$ | 1.0 g/l |
| | $Na_2SO_4$ | 1.8 g/l |
| | Urea | 2.0 g/l |
| | Citric acid | 2.0 g/l |
| | Trace metal sol. I* | 0.5 ml/l |
| | Pluronic ® | 0.1 ml/l |
| | pH 6.0 with 5 N NaOH | |
| | After sterilization: 20 g/l maltodextrin (MD01) | |

*)Trace metal solution I:
14.3 g/l   $ZnSO_4$ $7H_2O$
 2.5 g/l   $CuSO_4$ $5H_2O$
 0.5 g/l   $NiCl_2$ $6H_2O$
13.8 g/l   $FeSO_4$ $7H_2O$
 8.5 g/l   $MnSO_4$ $H_2O$
 3.0 g/l   Citric acid $H_2O$ To 250 ml polypropylene shake flasks without baffles containing 50 ml of ASP02 medium varying amounts of BS-protease are added in the form of a sterile filtrated solution. The shake flasks are inoculated with 1 ml of a spore suspension (approx. $10^5$ spores/ml) of *A. oryzae* (IFO 4177)

transformed with the expression plasmid pSX183 (the construction of which is further described below) and incubated at 300 rpm at the temperatures indicated in the examples. On day 4 the supernatant is analyzed for the presence of trypsin-like Fusarium protease.

Determination of trypsin-like Fusarium protease activity

The trypsin-like protease is assayed using the specific substrate N-Benzoyl-L-arginine p-nitroanilide hydrochloride (L-BAPNA, Sigma).

Buffer 0.01M dimethylglutaric acid (Sigma D4379), 0.2M boric acid and 0.002M calcium chloride adjusted to pH 6.5 with NaOH.

Substrate

L-BAPA is available from Sigma (B3133) or Merck (Art. 10754). A 0.2M stock solution in dimethyl sulfoxide is prepared (87 mg/ml) (store frozen) and diluted to 0.004M with the buffer described above.

Assay

The trypsin-like protease is diluted to approx. 15 µg/ml for the assay. 20 µl of the diluted trypsin-like protease are mixed with 200 µl of 0.004M L-BAPA in a 96 well microtiter plate. A blank with 20 µl buffer and 200 µl 0.004M L-BAPA is used for correction.

The absorption change (delta OD/min) is monitored at 405 nm in an Elisa reader for 10 minutes with readings every 5 minutes at 25° C. or room temperature. The result is calculated relative to the trypsin content of a reference Fusarium trypsin-like protease.

Determination of BS-protease activity

The activity of the BS-protease is determined with N,N-dimethyl casein (DMC) as a substrate. The primary amino groups formed in this process react with trinitrobenzene sulphonic acid forming a coloured complex. The reaction takes place for 9 minutes at 50° C., pH 8.3. The reaction is followed in situ in order that the change in absorbance (at 420 nm) per time unit can be calculated. The measuring time is 3 minutes. The change in absorbance is a measure of the reaction rate and the enzyme activity. The activity is determined relatively to an enzyme standard (e.g. a serine protease from Bacillus) and in the same units as for the standard. The unit is termed AU(H).

The N,N-dimethyl casein solution (0.4%) is prepared by dissolving 4.0 g of N,N-dimethyl casein in approx. 200 ml of boiling demineralized water during constant agitation for 20 minutes, mixing the resulting solution with a solution prepared from 11.92 g of Hepes buffer (Sigma H-3375) and 3.69 g of NaCl further comprising 9.0 ml of 4.0N NaOH and 1 mmole CaCl$_2$ and adding 1.5 ml of a Brij® 35 solution (150.0 g of Brij 35 (Atlas Chime) in 1000 ml of water).

An enzyme sample is made by mixing 0.5–1.0 g of the enzyme to be analysed with a 2% Na$_2$SO$_3$ solution (200 g Na$_2$SO$_3$, 15 ml of Brij® 35 solution, and 1 mmole CaCl$_2$, add up to 10 l of demineralized water) with an amount of the Na$_2$SO$_3$ solution resulting in a suitable enzyme concentration.

The 2,4,6-trinitrobenzene sulphonic acid solution (0.1%) reacting with the primary amino groups formed during the reaction is prepared by dissolving 200 mg of 2,4,6-trinitrobenzene sulphonic acid in 200 ml of demineralized water.

The BS-protease activity is determined from the reaction rates of standards and samples, which are determined as the increase in OD (slope) from 6 to 9 min. with measurements each 5 sec.

Determination of trypsin-like Fusarium protease by immunoelectrophoreses (RIE)

Enzymatically active trypsin-like Fusarium protease and the proform thereof are analyzed by RIE. Horizontal rocket immunoelectrophoresis is carried out in 1% agarose (Litex HSA/HSB, 1:1) with 20 µl antibody/ml. The vessel and gel buffer consists of 41 mM Tris (hydroxy methyl) aminomethane and 13 mM glycine buffer, pH 8.6. Electrophoresis is carried out for approx. 18 hours at 15° C., and 2 V/cm.

The antibody to be used in the process is raised against purified trypsin-like Fusarium protease in rabbits by standard procedures. Rabbits are immunized with purified protease, 250 µg/dose once a week for 10 weeks. Crude serum is used in the assays.

The active enzyme is found to migrate towards the positive pole, the proform towards the negative.

RESULTS

The results obtained for each set of fermentation conditions are shown in Table 1 below:

TABLE 1

| Medium | BS-protease AU(H)/l | Temperature | pH | Trypsin Proform mg/l | Mat. mg/l |
|---|---|---|---|---|---|
| ASP02 (minimal) | 0 | 34° C. | 6.1 | | 10 |
| | 0.5 | | 8.3 | | 80 |
| | 5.0 | | 6.4 | | (24) |
| | 0 | 30° C. | 5.7 | 53 | 20 |
| | 0.5 | | 7.1 | 0 | 132 |
| | 5.0 | | 6.0 | 0 | 147 |
| | 50.0 | | 7.5 | 0 | 163 |
| | 0 | 26° C. | 7.9 | | 47 |
| | 0.5 | | 7.9 | | 277 |
| | 2.5 | | 8.0 | | 311 |
| | 5.0 | | 8.1 | | 320 |
| | 20.0 | | 8.2 | | 300 |
| | 50.0 | | 8.1 | | 360 |
| FG4P (complex) | 0 | 34° C. | 7.1 | | 20 |
| | 0.5 | | 7.3 | | 26 |
| | 5.0 | | 7.3 | | 62 |
| | 0 | 30° C. | 6.7 | 0 | 70 |
| | 0.5 | | 6.8 | 0 | 60 |
| | 5.0 | | 6.8 | 0 | 108 |
| | 50.0 | | 6.9 | 0 | 176 |
| | 0 | 26° C. | 7.1 | | 142 |
| | 0.5 | | 7.2 | | 120 |
| | 5.0 | | 7.2 | | 192 |
| | 20.0 | | 6.5 | | 429 |
| | 50.0 | | 6.5 | | 393 |

The proform of the trypsin-like Fusarium protease (termed "Trypsin" in the table) has been estimated by RIE. The mature form has been estimated by RIE and the BAPNA-enzyme assay.

For the shake flash cultivated at 30° C., the proform as well as the mature enzyme are analyzed. From Table 1, it is apparent that in shake flasks comprising minimal medium and BS-protease, no proenzyme could be detected, whereas in shake flask without BS-protease 53 mg/l of the proenzyme is determined. These results indicate that the BS-protease is capable of cleaving the pro sequence of the enzyme.

By cultivation at 26° C. in complex medium comprising 20 AU(H)/l of BS-protease, 429 mg/l active or mature trypsin-like protease are obtained as compared to 142 mg/l by a control fermentation without BS-protease (corresponding to an increase of the yield of active enzyme of about 3 times). The level of mature trypsin-like protease is slightly lower in minimal medium, where the highest amount of product is 360 mg/l compared to 47 mg/l in the control (corresponding to an increase of the yield of active enzyme of about 8).

It is seen that the increase obtained by use of a process of the invention is significantly higher in minimal medium than in complex medium. It is contemplated that the A. oryzae host cell used for the production of the Fusarium trypsin-like protease itself produced a proteolytic enzyme capable of activating said trypsin-like protease. The apparent lower effect obtained in complex medium is probably due to the fact that a higher level of naturally-occurring maturating protease produced by A. oryzae is synthesized in complex medium. It should be emphasized that although the A. oryzae host cell presumably inherently produces an activated trypsin-like protease a substantial additional effect of adding the BS-protease during the fermentation is seen for the yield of active trypsin-like protease obtained.

Example 2: Enzyme Activation in a Model System

The ability of BS-protease to cleave the pro sequence from the proenzyme of the trypsin-like Fusarium protease is evaluated in a model experiment

MATERIALS AND METHODS

Enzyme activation in a model system

Dilutions of trypsin-like Fusarium protease proform as well as proteolytic enzyme solutions either comprising BS-protease or the naturally occurring F. oxysporum activating protease, p45, (the isolation of which is described in Example 4 below) is prepared in the BAPA-assay buffer (pH 6.5). 20 µl of a trypsin-like proenzyme dilution containing approx. 15 mg/l are mixed with 100 µl of proteolytic enzyme solution in 96 well microtiter plates and incubated at 25° C. After 5 and 40 minutes of incubation, the amount of active or mature trypsin-like protease is assayed by using 100 µl of 0.008M L-BAPA-substrate and the method described above. To test for blind effect of the proteolytic enzyme in the BAPA-assay, 20 µl of buffer are used instead of trypsin-like Fusarium protease proform.

RESULTS

Fermentation supernatant from a shake flask fermentation of A. oryzae IFO 4177 transformed with the plasmid pSX183 in minimal medium without addition of BS-protease is used. The supernatant contained 90 mg/l of the trypsin-like protease proform.

Dilutions with 18 mg/l proenzyme are incubated with three different concentrations of BS-protease (0, 0.5, and 5 AU(H)/l). The amount of active trypsin-like protease produced is measured after 5 and 40 minutes. The results, which are summarized in Table 2, show that the BS-protease is capable of cleaving the pro sequence of the proenzyme of the trypsin-like protease, resulting in active trypsin-like protease. Further, it is demonstrated that there is no blind effect of the BS-protease in the assay. A change in the concentration of active or mature enzyme during the assay period will influence the results of analysis and in these cases only rough estimates (illustrated by "~") are given.

TABLE 2

| Proenzyme mg/l | BS-protease AU/l | Mature enzyme mg/l | |
|---|---|---|---|
| t = 0 min. | t = 0 min. | t = 5 min. | t = 40 min. |
| 18 | 0 | 0 | 0.2 |
| 18 | 0.5 | ~1.7 | ~9.0 |
| 18 | 5.0 | ~12.1 | 18.3 |
| 0 | 5.0 | 0.1 | 0.0 |

Example 3: Stability of Enzyme and Proenzyme in Fermentation Broth

Materials and Methods

Evaluation of the Stability of Trypsin-like Fusarium Protease

The stability of the active trypsin-like Fusarium protease is evaluated by incubation at 30° C. of a supernatant of broth from a fermentation in complex medium of A. oryzae transformed with the plasmid pSX183 and sampling at relevant intervals. The transformant and the medium are described in the Materials and Methods section of Example 1.

Production of Crude Trypsin-like Fusarium Protease Proenzyme

Crude proenzyme is prepared from fermentation of A. oryzae (IFO 4177) transformed with the plasmid pSX183 described in the Materials and Methods section of Example 1 under conditions where proform is obtained: 500 ml shake flasks without baffles containing 100 ml YDP (10 g/l Bacto yeast extract, 20 g/l Bacto peptone, 30 g/l dextrose) are inoculated with approximately $10^6$ spores of the A. oryzae culture and incubated at 125 rpm at 26° C. for 2 days. Cell material is removed by filtration and crude proform is prepared from the medium by ultrafiltration and subsequent freeze-drying.

Evaluation of Stability and Activation of Trypsin-like Fusarium Protease Proenzyme The stability/maturation of proenzyme is evaluated by addition of crude proenzyme (approx. 100 mg/l) to the fermentation supernatant mentioned above, incubation at 30° C. and sampling at relevant intervals.

Results

The stability at 30° C. of active trypsin-like protease in a supernatant of fermentation broth of A. oryzae transformant (IFO4177/pSX183) is shown in Table 3.

TABLE 3

| Incubation time at 30° C. | 0 | 45 min | 4 hours | 20 hours |
|---|---|---|---|---|
| Trypsin[1] mg/ml | 75 | 76 | 74 | 66 |
| % residual activity | =100 | 101 | 99 | 88 |

[1]Activity is etimated by the BAPNA-assay. No proform is detected in the fermentation.

The results in Table 3 indicate that the mature enzyme is rather stable in the fermentation broth. Thus, after four hours, substantially no activity is lost, and after 20 hours, only about 10% is lost.

The stability and maturation of the trypsin-like protease proenzyme has been evaluated by the addition of 100 mg/l of crude proenzyme to the fermentation broth mentioned in Table 3. The results are shown in Table 4.

TABLE 4

| Incubation time at 30° C. | 0 | 15 min | 30 min | 45 min |
|---|---|---|---|---|
| Δ Mat. trypsin[1] (from proform) mg/l | 0 | 15 | 38 | 51 |
| Residual proform[2] mg/l | 98 | 71 | 23 | 1 |

[1]Values have been corrected for amount of trypsin in the fermentation supernatant itself.
[2]Proform is activated with an activating enzyme isolated from fermentation supernatant with *F. oxysporum* DSM 2672 and then estimated by the BAPNA-assay. Values has been corrected for the amount of mature enzyme measured in parallel.

From the results in Table 4, it is noticed that *A. oryzae* (IFO 4177) is capable of activating the proform. Besides it is obvious, that the proform is unstable in the fermentation broth. Haft of the added proform is converted to an active enzyme, the other haft is degraded.

Example 4: Isolation and Characterization of the p45 Proteolytic Enzyme From *Fusarium oxysporum*

Materials and Methods
Purification

*F. oxysporum* broth is centrifuged at 9000 rpm for 10 min. and the supernatant is filtered through a 0.45 µm filter. 200 ml of filtrate is concentrated down to 0 ml on an Amicon cell (PM 10 membrane) and Centriprep-0 (Amicon). 5 ml of concentrate is diluted to 100 ml and pH adjusted to 5 with acetic acid and run on a 1 ml MonoS column in the following buffer: 0.1M borate, 10 mM DMG, 2 mM calcium chloride, pH 5.2 in a gradient of 0–>0.5M sodium chloride over 70 min., after 10 min. of wash in the above-identified buffer at a flow rate of 1 ml/min; 1.5 ml fractions are collected and concentrated on Centricon-10 (Amicon).

Gel filtration using Superose12 (HR 10/30, Pharmacia) is performed in 0.1M borate, 10 mM DMG, 2 mM $CaCl_2$, pH 6.5, flow rate: 0.4 ml/min; 0.4 ml fractions are collected; 200 µl samples are injected.

Proteolytic enzyme assay

Proteolytic enzyme activity is measured as released trypsin activity from the recombinant proform of pro-trypsin-like *Fusarium oxysporum* protease disclosed in Example 1, supra after a 30–60 min pre-incubation at 37° C. in 0.1M Tris, 2 mM $CaCl_2$, pH 7 (at lower pH, 100 mM borate, 10 mM DMG, 2 mM $CaCl_2$ is used). The tryptic activity is measured in microtiter plates; 100 µl samples are mixed with 100 µl of substrate (Stock: 87 mg/ml L-BAPNA (Sigma) in DMSO, diluted 50-fold in buffer) and the absorption at 405 nm is measured using a Thermomax microplate reader from Molecular Devices.

SDS-PAGE and electroblotting onto PVDF

SDS-PAGE (10–27%, Novex) is run according to the manufacturer's instructions; samples to be run are preincubated with PMSF before adding sample buffer. Electroblotting onto pro-blot membranes (Applied Biosystems) is done in 3 mM $Na_2CO_3$, 10 mM $NaHCO_3$, 20% MeOH, pH 9.9 at 30 V for 2 hours using the blotting module from Novex. The pro-blot is stained as described by Applied Biosystems.

IEF-overlay

IEF (Ampholine PAG-plate: pH 3.5–9.5, Pharmacia) is run and stained according to the manufacturer's instructions. The gel to be overlaid is first equilibrated for 15 min in 0.1M Tris, 2 mM $CaCl_2$, pH 8.1 and then overlaid with 10 ml 1% agarose, 0.1M Tris, 2 mM $CaCl_2$, pH 8.1 added 300 µl L-BAPNA stock and 500 gl recombinant pro-trypsin-like *Fusarium oxysporum* protease disclosed in Example 1, supra (~0.25 mg/ml).

Amino acid analysis and amino acid sequencing

Microwave facilitated vapor phase hydrolysis of lyophilized samples is done using the MDS-2000 hydrolysis-station (CEM). 6N HCl containing 1% phenol (scavenger) is used for creating the vapor phase. Hydrolysis time is 20 min at 70 psi (~148° C.). Hydrolyzed samples are lyophilized and redissolved in 20 µl of 500 pmol/µl sarcosine and norvaline as internal standard. The analysis is done using the AminoQuant from Hewlett-Packard according to manufacturer's instructions; 1 µl of sample is injected. Amino acid sequencing is done using the 476A Protein Sequencer from Applied Biosystems according to manufacturer's instructions; premixed buffers are used for the online-HPLC.

RESULTS

Purification of p45 from *F. oxysporum* Broth

The p45 proteolytic enzyme is purified from concentrated and filtered fermentation broth, by using cation-exchange chromatography (MonoS) followed by gel filtration on Superose12. Fractions from MonoS are selected by assaying for proteolytic enzyme activity as release trypsin-like activity from pro-trypsin-like *Fusarium oxysporum* protease disclosed in Example 1, supra. Proteolytic enzyme containing fractions form the Superose12 column are identified by using the same assay procedure as for the MonoS-fractions. The purified proteolytic enzyme appears as a single band on SDS-PAGE at 45 kDa. Two isoforms of the maturase are observed in IEF (pH 3.5–9.5) at respectively pI 8.4 and 8.7.

Figure 2:
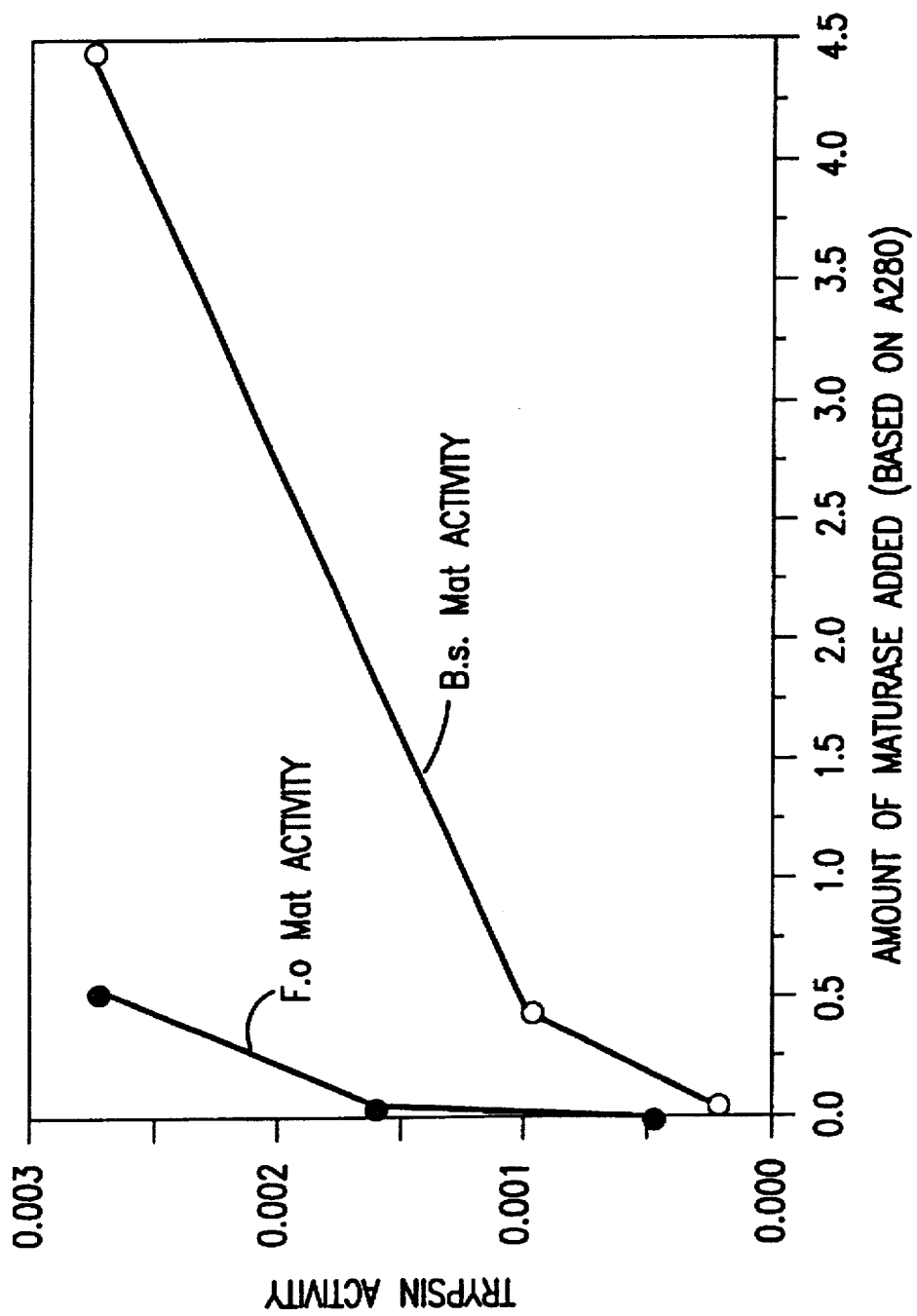
FIG. 2 shows a comparison of *F. oxysporum* proteolytic enzyme activity with that of Bacillus maturase used to process pro *F. oxysporum* protease.
Figure 4:
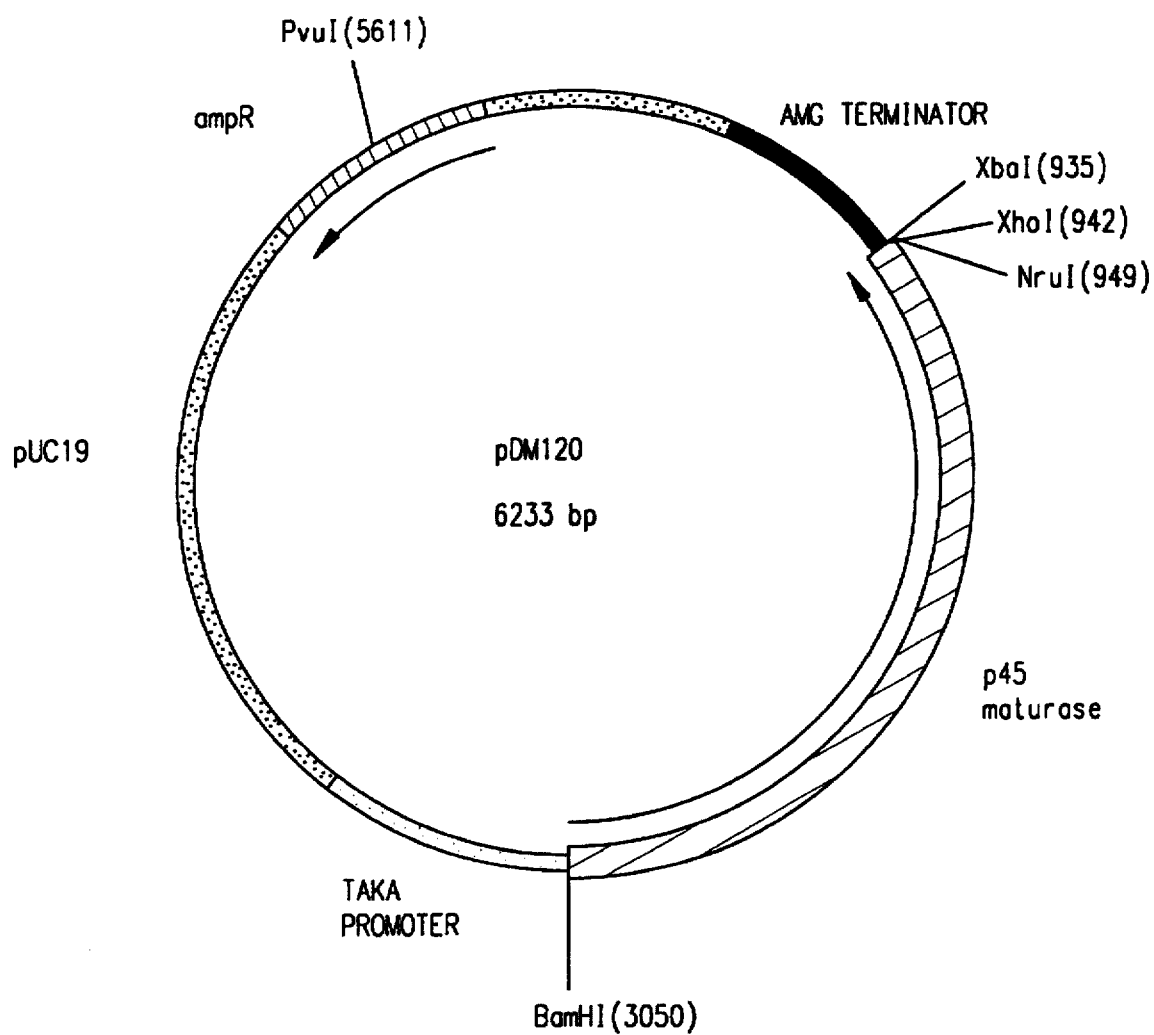
Figure 5:
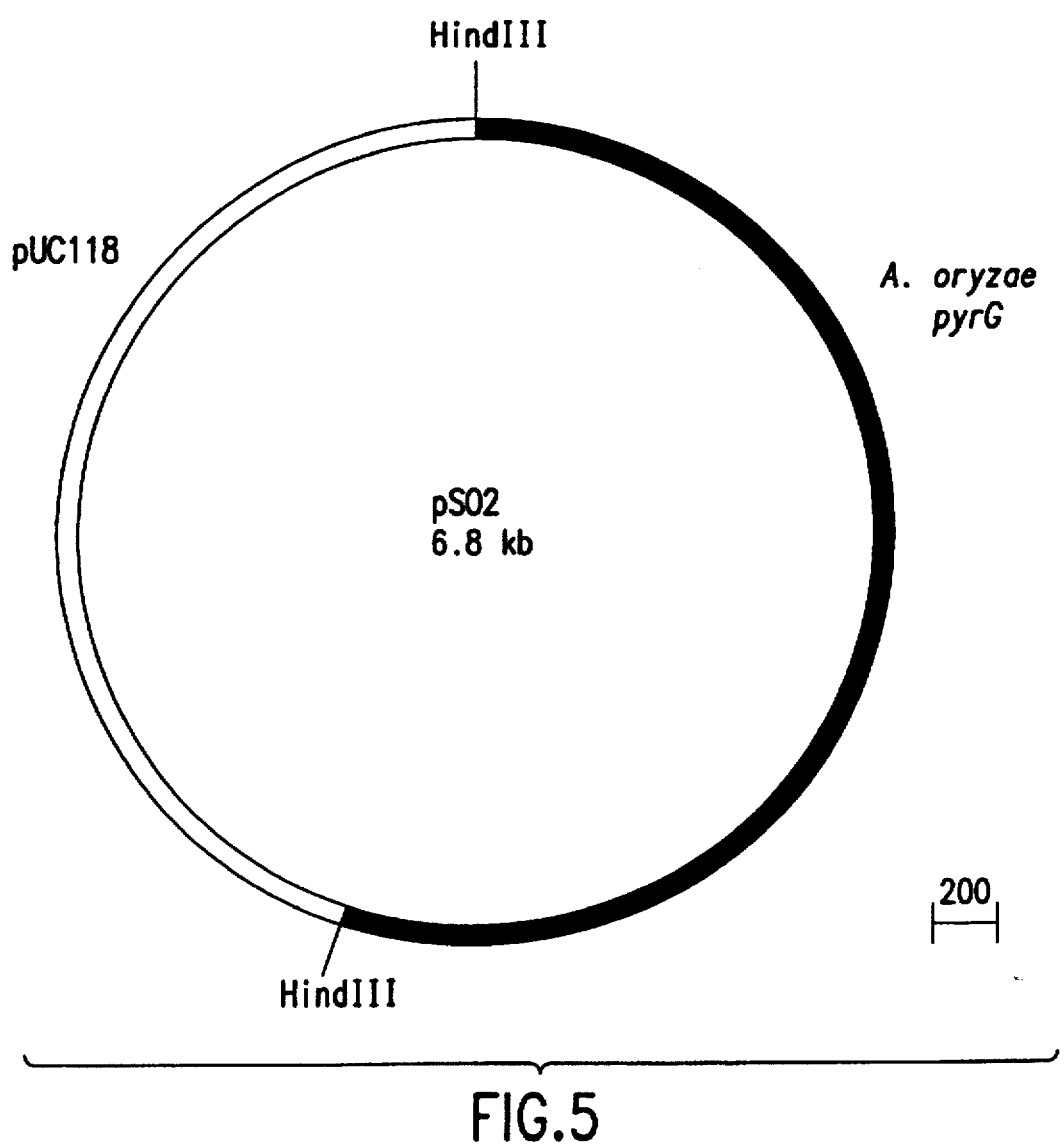
Figure 6:
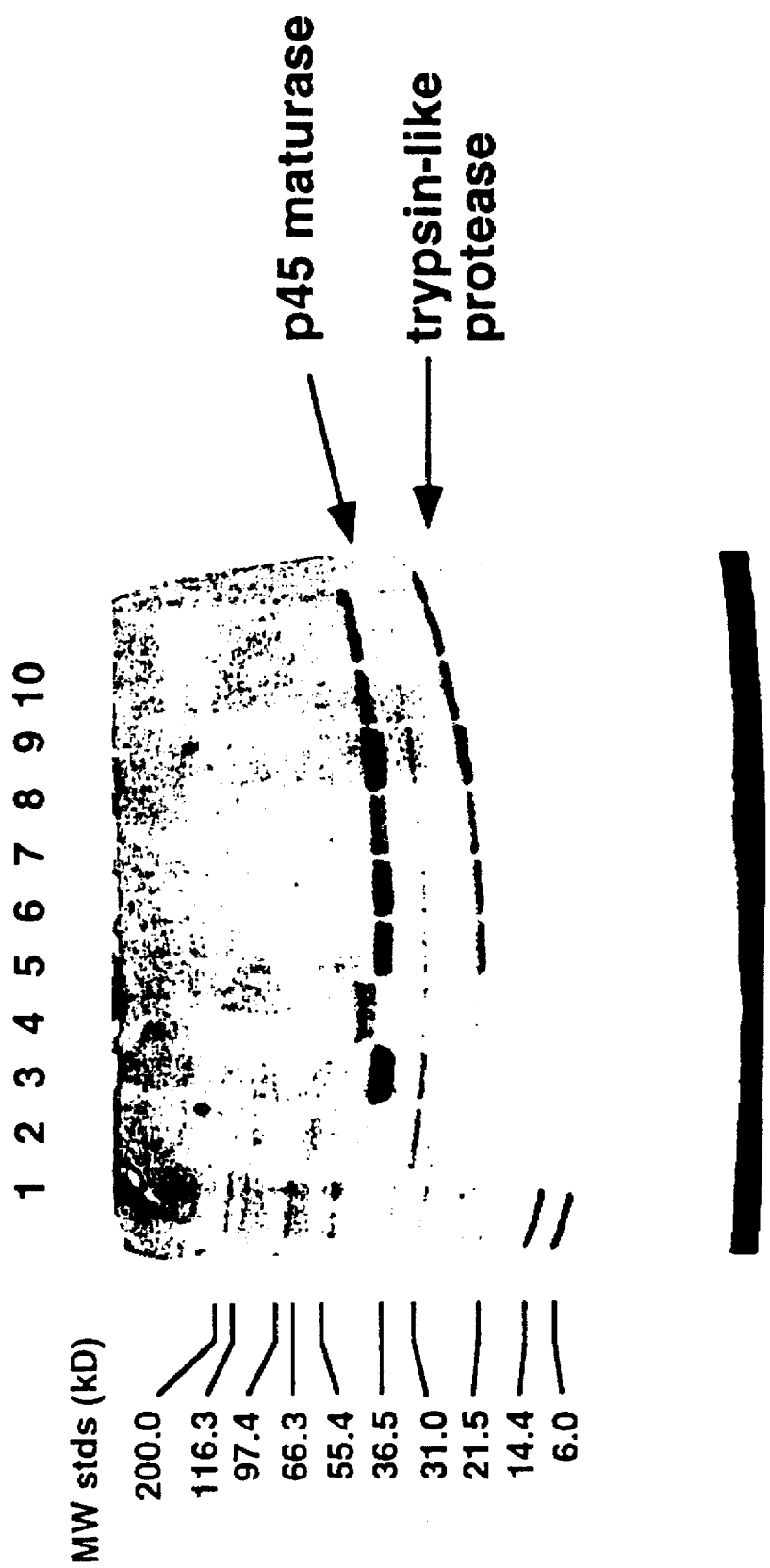

Results from amino acid analysis indicate that this proteolytic enzyme (p45) has the N-terminal amino acid sequence shown in the Sequence Listing as SEQ ID NO:3. Purified *F. oxysporum* p45 (maturase) demonstrates a high specific activity The desired proteolytic enzyme (maturase) fractions from the gel filtration column are pooled and loaded onto a preparative IEF apparatus. Samples are run at 1000V for 1 hour after the amperage had stabilized and then at 500V for another 30 minutes before 30 fractions of 3 ml each are collected. Only one fraction contained the proteolytic enzyme as seen on SDS-PAGE. A comparison of the activity of p45 with Bacillus maturase is shown in FIG. 2.

The p45 maturase is a metalloprotein

Metalloproteases contain a catalytic zinc metal center which participates in the hydrolysis of the peptide backbone. The active zinc center differentiates these proteases from calpains whose activities are dependent upon the presence of calcium. Confirmation of a protease as a metallo-protease is loss of proteolytic activity accomplished by removal of the zinc center with 1,10-phenanthroline (1 mM) followed by titration with $Zn^{2+}$(0.1–100µM) to restore full activity.

Table 5 demonstrates that the trypsin-like *Fusarium oxysporum* protease disclosed in the Materials and Methods section of Example 1, supra is not inhibited by 1,10-phenanthroline since similar tryptic activities result with or without inhibitor addition, $33.8\times10^{-4}$ and $34.0\times10^{-4}$ ΔAbs/min respectively. Recombinant protrypsin-like *Fusarium oxysporum* protease disclosed in Example 1, supra or *Fusarium oxysporum* maturase samples alone do not contain any tryptic activity (Table 1), however, when combined the maturase cleaves recombinant pro-trypsin-like *Fusarium oxysporum* protease disclosed in the Materials and Methods section of Example 1, supra to yield the active tryptic protease. Maturase activity is halted upon the addition of 1 mM 1,10-phenanthroline (Table 5). However, full reactivation of the Fusarium maturase occurs upon addition of 1 mM $Zn^{2+}$. Analogous results occur when EDTA (1 mM) is substituted for 1,10-phenanthroline.

TABLE 5

Inhibition of Fusarium Maturase with 1,10-Phenanthroline.

| Protein | 1,10-phenanthroline (1 mM) | $Zn^{2+}$ (1 mM) | Tryptic Activity (Δ Abs/min × $10^{-4}$) |
|---|---|---|---|
| Trypsin-like F. oxysporum protease | – | – | 34.0 |
| Trypsin-like F. oxysporum protease | + | – | 33.8 |
| Pro-trypsin-like-F. oxysporum protease | – | – | 1.26 |
| p45 Maturase | – | – | 1.33 |
| Pro-trypsin-like F. oxysporum protease + p45 Maturase | – | – | 54.0 |
| Pro-trypsin-like F. oxysporum protease + p45 Maturase | + | – | 2.9 |
| Pro-trypsin-like F. oxysporum protease + p45 Maturase | + | + | 50.6 |

Example 5: Cloning of the *Fusarium oxysporum* p45 GENE

A portion of the *F. oxysporum* p45 gene is first cloned by PCR. One primer is designed using the N-terminal protein sequence (SEQ ID NO:4) and a reverse primer is designed from an internal maturase peptide sequence (SEQ ID NO:5). PCR is performed using the DNA primers and genomic DNA isolated from *Fusarium oxysporum*. Genomic DNA is isolated as follows. Approximately 15 g wet weight *F. oxysporum* is grown in MY50 medium (50 g/l maltodextrin, 2 g/l $Mg_2SO_4$, 10 g/l $KH_2PO_4$, 2 g/l citric acid, 10 g/l yeast extract, 2 g/l urea, 2 g/l $K_2SO_4$, 0.5 ml trace metal solution to pH=6 with 5N NaOH) at 30° C. Mycelia are suspended in 16 ml TE (10 mM Tris.HCl, 1 mM EDTA pH=8.0), at 30° C. Mycelia are suspended in 16 ml TE (10 mM Tris. HCl, 1 mM EDTA pH=8.0), split into two tubes, and ca. 12 g of 0.45–0.52 mm glass beads (Thomas Scientific) are added to each tube. The samples are alternately vortexed and iced for 30 second intervals until a noticeable viscosity breakdown occurs. The samples are vortexed two additional 30 second intervals. 2.5 ml 20% SDS is added to each sample. The samples are mixed by inversion, incubated 10 minutes at room temperature, and mixed again. Samples are spun 8 minutes at 3.5K, room temperature. Supernatants are combined in a 50 ml polypropylene tube. The sample is extracted with an equal volume of TE equilibrated with phenol:chloroform:isoamyl alcohol (25:24:1) then centrifuged 10 minutes at 10,000 rpm, 4° C. The supernatant is treated with 300 µl 10 mg/ml proteinase K for 30 minutes at 37° C. The DNA is phenol/chloroform/isoamyl alcohol (P/C/I) extracted as described above, ethanol precipitated and dissolved in 5 ml TE. The sample is treated with 150 µl 10 mg/l RNAase A for 15 minutes at 65° C., then 15 minutes at 37° C. The sample is treated again with proteinase K (100 µl 10 mg/ml for 1.5 hours at 37° C.) and then P/C/I extracted twice and ethanol precipitated. The DNA is spooled onto a bent pasteur pipet and transferred to 5 ml 80% ethanol. The sample is spun 3 minutes at 10,000 rpm. The DNA pellet is dried briefly, then dissolved in 1 ml TE.

PCR is used to clone a portion of the *F. oxysporum* p45 maturase gene as follows: 50–100 µg *F. oxysporum* genomic DNA is mixed with ca. 100 pmoles each of the synthetic PCR primer DNAs in 1×Taq buffer (Boehringer Mannheim) and a concentration of 100 µM each of dGTP, dATP, dTTP, and dCTP, in a volume of 50 µl. Taq DNA polymerase (Boehringer Mannheim), 1–5 units, is added and the PCR incubations are, 95° C. 5 min then 35 cycles of [95° C. 30 seconds: 50° C. 1 minute: 72° C. 1 min]. The PCR reaction produces two DNA fragments of ca. 1.0 and 1.3 kb in length. These fragments are isolated by gel electrophoresis, purified, cloned into an *E. coli* replicating plasmid, and sequenced using standard methods known in the art of molecular biology. The 1.0 kb DNA fragment is found to contain *F. oxysporum* p45 gene sequences by a comparison of the translations of the DNA with the amino acid sequences obtained from the direct protein sequencing. Therefore, this 1.0 kb PCR generated DNA fragment is used as a probe to clone the entire maturase gene from a *F. oxysporum* genomic DNA library.

A genomic DNA library in lambda phage is prepared from the *F. oxysporum* genomic DNA using methods such as those described found in Sambrook et al., 1989, Molecular Cloning: A Laboratory Manual, Cold Spring Harbor, N.Y. A total of 50 µg genomic DNA is digested in a volume of 200 µl containing 10 mM Tris (pH=7.5), 50 mM NaCl, 7 mM $MgCl_2$, 7 mM 2-mercaptoethanol, and 4 units restriction enzyme Sau3A for one minute at 37° C. Partially digested DNA of molecular size 10–20 kb is isolated by agarose gel electrophoresis, followed by electroelution into dialysis membrane and concentration using an Elutip-D column (Schleicher and Schuell). One µg of lambda arms of phage of EMBL4 that had been cut with restriction enzyme BamH1 and treated with phosphatase (Clonetech) is ligated with 300–400 µg Sau3A cut genomic DNA in a volume of 25 µl under standard conditions (see Sambrook et al., 1989, Molecular Cloning: A Laboratory Manual, Cold Spring Harbor, N.Y.). Lambda phage were prepared from this ligation mix using a commercially available kit (Gigapack Gold II, Stratagene) following the manufacturers directions. The plating of ca. 18,000 recombinant lambda phage and the production of filter lifts (to N+filters, Amersham) were performed using standard methods (Sambrook et al., 1989, Molecular Cloning: A Laboratory Manual, Cold Spring Harbor, N.Y.). The filters were processed for hybridization with a Genius Kit for non-radioactive nucleic acids detection (Boehringer Mannheim) using the instructions provided by the manufacturer. The DNA used as a p45 maturase probe is the 1.0 kb PCR fragment described above. The probe is labelled by PCR incorporation of dioxigenin (DIG) using a DIG labelling kit and the instructions supplied by the manufacturer. Fifteen ng of the 1.0 kb p45 fragment is mixed in 1×Taq Buffer (Boehringer Mannheim), 1×DIG labelling mix (Boehringer Mannheim) with 100 pmoles each N-terminal primer (SEQ ID NO:4) and internal reverse primer (SEQ ID NO:5), and 1–5 units Taq polymerase (Boehringer Mannheim) in a total volume of 80 µl. Reaction conditions were: 95° C. 3 minutes, 35×[95° C., 30 seconds; 50° C. 1 minute; 72° C., 1 minute], 72° C., 5 minutes. The filter hybridizations using the DIG labelled probe, and the wash conditions were performed using the instructions provided by the Genius Kit manufacturer.

Hybridizing phage are detected with an alkaline phosphatase-conjugated anti-digoxigenin antibody visualized with Lumiphos 530 as described by the manufacturer (Boehringer Mannheim). DNA preparations are made from the positive lambda clones using the Qiagen Lambda Midi Kit (QIAGEN,Inc.). DNA from one preparation is digested with restriction enzyme EcoRI and a 6.3 kb fragment is subcloned into plasmid pUC118. DNA sequence analysis of portions of this subclone identified the entire coding region of the p45 gene (see FIG. 3 and SEQ ID NO:6).

Cloning p45 cDNA

Total RNA and Poly-A RNA is prepared from *F. oxysporum* according to previous published protocols (Chirgwin et al. Biochemistry 18:5294–5299 (1989), Aviv and Leder, Proceedings of the National Academy of Sciences, USA 69:1408–1412 (1972), Sambrook et al., 1989, Molecular Cloning: A Laboratory Manual, Cold Spring Harbor, N.Y.) with the following modifications. Specifically, mycelia is ground in liquid nitrogen to a fine powder and then resuspended, with stirring, in a lysis buffer containing 4M guanidinium thiocyanate, 0.5% Na-laurylsarcosine, 25 mM Na citrate, and 0.1M 2-mercaptoethanol, pH=7.0, for 30 minutes at room temperature. Cell debris is removed by low speed (5000 rpm for 30 minutes) centrifugation. Typically, the poly-A RNA fraction is isolated using oligo(dT) cellulose obtained from Boehringer Mannheim.

The polyA RNA is used to generate cDNA using the hairpin/RNaseH method (Sambrook et al., 1989, Molecular Cloning: A Laboratory Manual, Cold Spring Harbor, N.Y.).

Specifically, 5 μg polyA RNA in 5 μl water is heated at 70° C. then placed on ice. A total reaction mix of 50 μl is prepared containing the polyA RNA, 50 mM Tris(pH=8.3), 75 mM KCl, 3 mM $MgCl_2$, 10 mM DTT, 1 mM each dGTP dATP dTTP and dCTP, 40 units RNasin 10 μg oligo(dT12-18) primer, and 1000 units SuperScript II RNase H- reverse transcriptase (Bethesda Research Laboratories). The mix is incubated at 45° C. for one hour. Then 30 μl of 10 mM Tris(pH=7.5) 1 mM EDTA, 40 μg glycogen carrier (Boehringer Mannheim), 0.2 volumes 10M ammonium acetate, and 2.5 volumes ethanol were added to precipitate the nucleic acids. After centrifugation, the pellet is resuspended in 20 mM Tris(pH=7.4), 90 mM KCl, 4.6 mM $MgCl_2$, 10 mM ammonium sulphate, 16 μM βNAD+, 100 μM each dGTP dATP dTTP dCTP, 44 units *E. coli* DNA polymerase I, 6.25 units RNaseH, and 10.5 units DNA ligase. Second strand DNA synthesis is performed in this solution at 16° C. for 3 hours. The DNA is concentrated by ethanol precipitation and the pellet is resuspended in 30 μl of 30 mM Na-acetate (pH=4.6), 300 mM NaCl, 1 mM $ZnSO_4$, 0.35 mM DTT, 2% glycerol, and 30 units Mung Bean nuclease (Bethesda Research Laboratories) at 30° C. for 30 minutes. The DNA solution is neutralized with 70 μl 10 mM Tris(pH=7.5) 1 mM EDTA, phenol extracted, and ethanol precipitated. The pellet is treated with 7.5 units T4 polymerase (Invitrogen) at 37° C. for 15 minutes in 50 μl buffer (20 mM Tris-acetate pH=7.9, 10 mM Mg-acetate, 50 mM K-acetate, 1 mM DTF, 0.5 mM each dGTP dATP dTTP dCTP). The reaction is stopped by addition of EDTA to 20 mM followed by phenol extraction and ethanol precipitation. The result of this procedure is double stranded cDNA with blunt ends suitable for attachment of DNA linkers and cloning into any vector.

The cDNA with EcoR1 linkers is size fractionated on an agarose gel to obtain cDNAs of molecular size 0.7 kb or greater. The cDNA is recovered from the gel by electroelution and purified by phenol extraction and ethanol precipitation. The size fractionated cDNA is used to construct a lambda cDNA library. The cDNA is cloned into lambda ZIPLOX arms (Gibco BRL). Full length cDNA lambda clones are identified using a 467 bp digoxigenin labeled fragment as probe (bp 336–803 of the genomic clone) with the techniques of plaque lifts and DNA hybridizations as previously described. Full length cDNA is recovered in plasmid pZL1as described by the manufacturer (strains and plasmid from Gibco BRL). The full length cDNA is sequenced and compared with the sequence of the genomic DNA. The genomic DNA is 2049 bp in length and contains three introns. The predicted coding region of prepro-p45 protease consists of a putative 18 amino acid signal sequence, a 226 amino acid pro-region, and a 388 amino acid mature region is shown in SEQ ID NO:6 and in FIG. 3.

Example 6: Coexpression of Both p45 Proteolytic Enzyme and the Trypsin-Like Protease in the Same Microorganism Host (*A. oryzae*)

In the example described herein, another disclosure of maturation of the trypsin-like protease is set forth.

A 2102 bp BamHI/NruI genomic prepro-p45 protease fragment is inserted between a TAKA amylase promoter and amyloglucosidase (AMG) terminator. To accomplish this, the 5'-end of the gene is modified using PCR techniques to introduce a BamHI site directly upstream of the ATG initiation codon. At the 3'-end of the gene, the endogenous NruI site 44 bp downstream from the termination codon is used. The p45 expression plasmid is called pDM120 (FIG. 4). A pyrG- *A. oryzae* host strain is co-transformed with plasmids pDM120 and pSO2. Plasmid pSO2 contains the *A. oryzae* pyrG marker (see FIG. 5).

The transformation of *A. oryzae* is performed by the protoplast method (Christensen et al. Biotechnology 6:1419–1422 (1988), Yelton et al. Proceedings of the National Academy of Sciences (USA) 81: 1470–1474 (1984)). Typically, *A. oryzae* mycelia are grown in a rich nutrient broth. The mycelia are separated from the broth by a technique such as filtration, centrifugation, etc. The enzyme preparation Novozyme® (Novo Nordisk) is added to the mycelia in osmotically stabilizing buffer such as 1.2 M $MgSO_4$ buffered to pH=5.8 with sodium phosphate. The suspension is incubated for 60 minutes at 30° C. with agitation. The protoplasts are harvested and the protoplasts are resuspended in a osmotically stabilizing buffer containing calcium such as STC (1.2M sorbitol, 10 mM $CaCl_2$, 10 mM Tris-HCl pH=7.5). Transforming DNA is added to ca. 100 μl protoplast suspension and then 200 μl PEG solution (60% PEG 4000, 10 mM $CaCl_2$, 10 mM Tris.HCl, pH=7.5 is added and the mixture is incubated for 20 minutes at room temperature. An additional 1 ml. PEG solution is added and the solution is incubated again for 20 minutes at room temperature. The transformed protoplasts are diluted with 8 ml STC buffer and plated to selective plates. Acetamide (as sole nitrogen source for growth) plates can be used to select for transformants containing an exogenously supplied amdS marker. Minimal plates can be used for transformants containing an exogenously supplied pyrG gene.

Transformants are grown in M400Da medium (maltodextrin, 50.0 g/L; $MgSO_4.7H_2O$, 2.0 g/L; $KH_2PO_4$, 2.0 g/L; citric acid, 4.0 g/L; yeast extract, 8.0 g/L; urea, 2.0 g/L; trace metals solution (as described earlier), 0.5 ml/L; pH=6.0 with 5N NaOH) at 37° C. and the broths analyzed for the production of p45 by SDS/PAGE. A major band migrating at ca. 45 kD is seen in at least one transformant, strain DLM7, and no p45 is seen in control cultures. The recombinant p45 produced in DLM7 is analyzed by protein sequence analysis and the N-terminal residues match the mature N-terminus of p45 produced from *F.oxysporum*. Therefore, the p45 is processed correctly when made in *A. oryzae*.

In order to make a host organism that expresses both the p45 and the trypsin-like protease, strain DLM7 is co-transformed with plasmids pSX233 containing the trypsin-like protease and pToC90 containing the *A. nidulans* amdS gene as a selectable marker. Plasmid pSX233 is a derivative of plasmid pSX183 in which the DNA linker at the beginning of the precursor trypsin-like protease gene has been changed from GGATCCTCGAATTCTCTTCA-GATCTCTTCACCATGG (SEQ ID NO:7) to GGATCCAC-CATGG (SEQ ID NO:8) using standard techniques of molecular biology. The underlined ATG indicates the position of the initiator methionine codon. Co-transformants are grown in FG4P medium and analyzed for *F. oxysporum* trypsin-like protease activity using the L-BAPNA assay. Six of the transformants made significantly more trypsin-like protease than a control strain that did not contain the p45. Supernatants from these transformant cultures (and controls) are analyzed by SDS/PAGE (FIG. 6). All transformants showed the production of both trypsin-like protease and p45 maturase from the same host organisms. The results show that co-expression of the (precursor) trypsin-like protease and the *F. oxysporum* p45 maturase in the same host cells (*A. oryzae*) results in significantly enhanced expression of active trypsin-like protease.

Example 7: Purification and Initial Characterization of a Neutral Metalloprotease (npI) from *Aspergillus oryzae*

MATERIALS AND METHODS

Purification

A 10 l *A. oryzae* 1560 (7C1-58) fermentation is harvested. 9 l of broth is obtained and filtered through a 0.1 μm hollow fibre (Amicon) and concentrated to 700 ml on a 3 kDa cut off spiral ultrafiltration cartridge (Amicon).

300 ml is diluted to 1000 ml (<1.5 mS, pH 7.1) and loaded onto a 150 ml (2.6 cm i.d.) Q-Sepharose column equilibrated in 0.1 borate, 10 mM DMG, 2 mM $CaCl_2$, pH 6.2 at a flow rate on 5 ml/min. The column is washed with buffer and eluted with a 0–>1M NaCl gradient in 1050 ml at 6 ml/min. 12 ml fractions are collected and assayed for maturase activity for pro-trypsin-like *Fusarium oxysporum* protease disclosed in Example 1, supra, maturing activity. Maturase containing fractions are pooled and concentrated on a YM3 membrane.

The pool is then diluted to 80 ml (<1.5 mS, pH 7.5), loaded onto a 20 mi MonoQ-column (1.6) cm i.d.) equilibrated in 20 mM Tris, 2 mM $CaCl_2$, pH 7.5 and eluted in a 0–>0.5M NaCl gradient in 300 ml at a flow rate on 6 ml/min). 4.5 ml fractions are collected and tested for maturase activity. Fractions having activity are pooled and concentrated on Centriprep-10.

3 ml of MQ1 is subjected to gel filtration using a HiLoad Superdex 200 16/60 column equilibrated in 100 mM borate, 10 mM DMG, 2 mM $CaCl_2$, pH 6.2 at a flow rate of 1 ml/min. 1 ml fractions are collected. Fractions having maturase activity are pooled.

A further purification step is established by doing pilot runs on either phenyl-superose 5/5 (flow rate 0.5 ml/min, 1.7–>OM $(NH_4)_2SO_4$ gradient in 60 min in 25 mM Tris pH 7, 1 ml fractions collected) or bacitracin coupled to CH Sepharose 4B (15 ml column 1.6 cm i.d., flow rate: 2 ml/min, 0–>100% B in 80 min (A: 25 mM acetate, pH 5, B: 0.1M Tris, 1M NaCl, 25% isopropanol, pH 7.5), 3 mL fractions collected). 2 ml of S2 is desalted on PD-10 for each run (eluted in 3.5 ml of the respective buffers), 3 ml is loaded. Fractions having maturase activity are pooled. A larger amount is purified using the bacitracin-column; 3 ml S12+3 ml S13+1 ml S2 is desalter on PD-10 into 25 mM acetate, pH 5 and 10 ml is loaded on the column. Fractions having maturase activity are pooled and concentrated on Centricon-10 and Microcon-10).

Coupling of bacitracin

Coupling of bacitracin to activated CH Sepharose 4B (Pharmacia) is performed according to manufacturer's descriptions. 6.6 g CH Sepharose (swell in 1 mM HCl and ished in coupling buffer) is used and coupled with 0,25 g (18250 units) of bacitracin (Sigma) in 0.1M $NaHCO_3$, 0.5M NaCl, pH 8 for 2 hours at room temperature. Excess active groups are blocked with 0.1M Tris, pH 8 followed by washing with 0.1M acetate, 0.5M NaCl, pH 4.

Maturase assay

Maturase activity is measured as released trypsin activity from pro-trypsin-like *Fusarium oxysporum* protease disclosed in Example 1, supra (~25 μg/ml) after a 30 min pre-incubation at 37° C. in 0.1M Tris, 2 mM $CaCl_2$ pH 7.5 (at lower pH either borate/DMG or acetate buffer containing $CaCl_2$ is used). The tryptic activity is measured in microtiter plates: 100 μl of substrate (Stock: 87 mg/ml L-BAPNA (Sigma) in DMSO, diluted 50 fold in buffer) and the absorption at 405 nm is measured using Thermomax microplate reader from Molecular Devices.

SDS-PAGE and Electroblotting onto PVDF SDS-PAGE (10–27%, Novex) are run according to the manufacturer's instructions (125 V, 2 hours); samples to be run is preincubated with PMSF (0.2%) before adding sample buffer. Electroblotting onto pro-blot membranes (Applied biosystems) is performed in 3 mM $Na_2CO_3$, 10 mM $NaHCO_3$, 20% MeOH, pH 9.9 at 25V for 2.5 hours using the blotting module from Novex. The pro-blot is stained as described by Applied Biosystems.

IEF-overlay

IEF (Ampholine PAG-plate: pH 3.5–9.5, Pharmacia) is run (1500V, 50 mA, 1.25 hour) and stained according to the manufacturer's instructions. The gel to be overlaid is first equilibrated for 15 min in 0.1M Tris, 2 mM $CaCl_2$, pH 7 and then overlaid with 1% agarose, 0.1M Tris, 2 mM $CaCl_2$, pH 7 added L-BAPNA stock (50-fold diluted) and pro-trypsin-like *Fusarium oxysporum* protease disclosed in Example 1, supra (crude concentrated broth 1 mg/ml, 50 fold diluted). Casein overlay is done by having 1% skimmed milk in the overlay buffer.

Amino acid sequencing

Amino acid sequencing is done using the 476A Protein Sequencer from Applied Biosystems according to manufacturer's instructions; premixed buffers are used for the online-HPLC.

RESULTS

The purification procedure described supra results in a more than 3300 fold purification (purity>95% (SDS-PAGE). The purified npI has a molecular weight around 46 kDa from SDS-PAGE and a pI around 4.5 from IEF. An overlaid IEF-gel (overlaid with pro-trypsin-like *Fusarium oxysporum* protease disclosed in Example 1, supra and L-BAPNA) shows that the maturase activity occur around pI 4.5, where casein clearing is also seen. When the purified npI is subjected to N-terminal amino acid sequencing, one sequence is obtained (the first few cycles contained some background). This amino acid sequence corresponds to the N-terminal amino acid sequence obtained from the 46 kDa band blotted from an SDS-gel on a PVDF-membrane; giving the amino acid sequence reported in FIG. 7. The N-terminal amino acid sequence is 64% homologous to the N-terminal sequence for p45 from *F. oxysporun* (FIG. 7). The protease pH-optimum is found to be around 5.5–6.0. Incubations with pro-trypsin-like *Fusarium oxysporum* protease disclosed in Example 1, supra are done in dilute buffers at various pHs.

DEPOSIT OF MICROORGANISMS

The following biological materials have been deposited in the Agricultural Research Service Patent Culture Collection (NRRL), Northern Regional Research Center, 1815 University Street, Peoria, Ill., 61604, USA.

| Strain | Accession Number | Deposit Date |
|---|---|---|
| E. coli containing pDM120 (p45 maturase) (EMCC 0099) | NRRL B-21239 | 4/21/94 |
| E. coli containing pSO2 (pyrG) (EMCC 0100) | NRRL B-21240 | 4/21/94 |
| E. coli containing pSX233 (EMCC 0101) | NRRL B-21241 | 4/21/94 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A process for producing an active trypsin-like *Fusarium oxysporum* protease by fermentation of a cell expressing the enzyme in the form of a proenzyme having an amino acid sequence of SEQ ID NO:2, in which the cell expressing the proenzyme has been transformed with a nucleic acid fragment containing a nucleic acid sequence encoding the proenzyme, which process comprises a. performing the fermentation in the presence of a proteolytic enzyme, in which said proteolytic enzyme is encoded by and expressed from a recombinant DNA sequence present in the cell from which the proenzyme is expressed, is different from the active enzyme and capable of converting the proenzyme into an active enzyme, and b. recovering the active enzyme from the fermentation broth.

2. The process according to claim 1, in which the nucleic acid sequence encoding the trypsin-like *Fusarium oxysporum* protease is obtained from a strain of the *F. oxysporum* deposited at the Deutsche Sammlung yon Mikroorganismen, Göttingen, Germany under the number DSM 2672.

3. The process according to claim 1 in which the proenzyme is expressed as a preproenzyme.

4. The process according to claim 1 in which the proteolytic enzyme is a metalloprotease, a serine protease, an aspartic protease, an alkaline protease subtilisin or a cysteine protease.

5. The process according to claim 1 in which the proteolytic enzyme is a metalloprotease obtained from a strain of the *F. oxysporum* deposited at the Deutsche Sammlung von Mikroorganismen, Göttingen, Germany under the number DSM 2672.

6. The process according to claim 1 in which the cell expressing the proenzyme is a microorganism.

7. The process according to claim 6, in which the microorganism is a bacterium or a fungus.

8. The process according to claim 6, in which the microorganism is a gram-positive bacterium.

9. The process according to claim 8 in which the gram-positive bacterium is of the genus Bacillus or Streptomyces.

10. The process according to claim 6, in which the microorganism is a gram-negative bacterium.

11. The process according to claim 10 in which the gram-negative bacterium is of the genus Escherichia.

12. The process according to claim 10 in which the microorganism is a yeast.

13. The process according to claim 12 in which the yeast is of the genus Saccharomyces.

14. The process according to claim 10 in which the microorganism is a filamentous fungus.

15. The process according to claim 14 in which the filamentous fungus is of the genus Aspergillus or Fusarium.

16. A host cell comprising a heterologous nucleic acid fragment containing a nucleic acid sequence encoding a trypsin-like *Fusarium oxysporum* protease in the form of a proenzyme having an amino acid sequence of SEQ ID NO:2, and a heterologous nucleic acid fragment containing a nucleic acid sequence encoding a proteolytic enzyme capable of converting the proenzyme into an active enzyme, the proenzyme being less stable than the active enzyme.

17. The host cell of claim 16 in which the host cell is a bacterium or fungal cell.

18. The host cell of claim 16 in which the nucleic acid sequence encoding the trypsin-like *Fusarium oxysporum* protease is integrated into the host cell genome.

19. The host cell of claim 16 in which the nucleic acid sequence encoding the proteolytic enzyme is integrated into the host cell genome.

20. The host cell of claim 16 in which the nucleic acid sequence encoding the trypsin-like *Fusarium oxysporum* protease is contained on a vector.

21. The host cell of claim 16 in which the nucleic acid sequence encoding the proteolytic enzyme is contained on a vector.

22. The host cell according to claim 16 which comprises a nucleic acid sequence encoding the amino acid sequence depicted in SEQ ID NO:2 and a nucleic acid sequence encoding the amino acid sequence depicted in SEQ ID NO:6.

23. A DNA construct comprising a DNA sequence encoding a trypsin-like *Fusarium oxysporum* protease in the from of a proenzyme having an amino acid sequence of SEQ ID NO:2 and a DNA sequence encoding a proteolytic enzyme capable of converting the proenzyme into an active enzyme, the proenzyme being less stable than the active enzyme.

24. A recombinant expression vector comprising the DNA construct of claim 23.

25. A process for producing an active enzyme by fermentation of a cell expressing the enzyme in the form of a proenzyme, in which the cell expressing the proenzyme has been transformed with a nucleic acid fragment containing a nucleic acid sequence encoding the proenzyme, which process comprises a. performing the fermentation in the presence of a metalloprotease having an amino acid sequence of SEQ ID NO:6 obtained from a strain of *F. oxysporum* in which said metalloprotease is encoded by and expressed from a recombinant DNA sequence present in the cell from which the proenzyme is expressed, is different from the active enzyme and capable of converting the proenzyme into an active enzyme, and b. recovering the active enzyme from the fermentation broth.

26. The process according to claim 25 in which the proteolytic enzyme is a metalloprotease obtained from a strain of the *F. oxysporum* deposited at the Deutsche Sammlung von Mikroorganismen, Göttingen, Germany under the number DSM 2672.

27. A host cell comprising a heterologous nucleic acid fragment containing a nucleic acid sequence encoding a proenzyme and a heterologous nucleic acid fragment containing a nucleic acid sequence encoding a metalloprotease having an amino acid sequence of SEQ ID NO:6 obtained from a strain of *F. oxysporum* capable of converting the proenzyme into an active enzyme, the proenzyme being less stable than the active enzyme.

28. A DNA construct comprising a DNA sequence encoding a proenzyme and a DNA sequence encoding a metalloprotease having an amino acid sequence of SEQ ID NO:6 obtained from a strain of *F. oxysporum* capable of converting the proenzyme into an active enzyme, the proenzyme being less stable than the active enzyme.

* * * * *